US012057232B2

United States Patent
Clifford et al.

(10) Patent No.: US 12,057,232 B2
(45) Date of Patent: Aug. 6, 2024

(54) PASSIVE DATA COLLECTION AND USE OF MACHINE-LEARNING MODELS FOR EVENT PREDICTION

(71) Applicants: EMORY UNIVERSITY, Atlanta, GA (US); GEORGIA TECH RESEARCH CORPORATION, Atlanta, GA (US)

(72) Inventors: Gari Clifford, Decatur, GA (US); Ayse Cakmak, Atlanta, GA (US); Amit Shah, Atlanta, GA (US); Erik Reinertsen, Atlanta, GA (US)

(73) Assignees: Emory University, Atlanta, GA (US); Georgia Tech Research Foundation, Atlanta, GA (US)

(*) Notice: Subject to any disclaimer, the term of this patent is extended or adjusted under 35 U.S.C. 154(b) by 522 days.

(21) Appl. No.: 17/295,248

(22) PCT Filed: Dec. 5, 2019

(86) PCT No.: PCT/US2019/064630
§ 371 (c)(1),
(2) Date: May 19, 2021

(87) PCT Pub. No.: WO2020/118022
PCT Pub. Date: Jun. 11, 2020

(65) Prior Publication Data
US 2021/0398683 A1     Dec. 23, 2021

Related U.S. Application Data

(60) Provisional application No. 62/777,029, filed on Dec. 7, 2018.

(51) Int. Cl.
*G16H 50/30*     (2018.01)
*G06F 18/2431*     (2023.01)
(Continued)

(52) U.S. Cl.
CPC ......... *G16H 50/30* (2018.01); *G06F 18/2431* (2023.01); *G16H 10/60* (2018.01);
(Continued)

(58) Field of Classification Search
CPC ........ G16H 50/30; G16H 40/67; G16H 20/30; G16H 10/60; G16H 50/20; G16H 40/60; G16H 20/00
See application file for complete search history.

(56) References Cited

U.S. PATENT DOCUMENTS

2014/0350436 A1   11/2014   Nathan et al.
2015/0213225 A1   7/2015   Amarasingham et al.
(Continued)

FOREIGN PATENT DOCUMENTS

WO    WO-2015157572 A1 * 10/2015 ............. G06Q 10/06

OTHER PUBLICATIONS

Churpek, Matthew M., et al. "Using electronic health record data to develop and validate a prediction model for adverse outcomes on the wards." Critical care medicine 42.4 (2014): 841. (Year: 2014).*
(Continued)

*Primary Examiner* — Jason B Dunham
*Assistant Examiner* — Constantine Siozopoulos
(74) *Attorney, Agent, or Firm* — Emory Patent Group

(57) ABSTRACT

Methods and systems for monitoring of sensor data for processing by machine-learning models to generate event predictions to estimate a risk a medical event are provided. An electronic device or wearable smart device may monitor the output of various sensors to collect data related to a person's activity level, location changes, and communications and may use this information as input to a personalized trained machine-learning model to predict a likelihood of an event.

27 Claims, 12 Drawing Sheets

(51) Int. Cl.
*G16H 10/60* (2018.01)
*G16H 40/67* (2018.01)
*G16H 50/20* (2018.01)
*G16H 50/70* (2018.01)

(52) U.S. Cl.
CPC ............. *G16H 40/67* (2018.01); *G16H 50/20* (2018.01); *G16H 50/70* (2018.01)

(56) References Cited

U.S. PATENT DOCUMENTS

| | | |
|---|---|---|
| 2015/0305632 A1 | 10/2015 | Najarian et al. |
| 2015/0370994 A1 | 12/2015 | Madan et al. |
| 2016/0113591 A1 | 4/2016 | Pijl et al. |
| 2016/0163174 A1 | 6/2016 | Zhang |
| 2017/0000422 A1 | 1/2017 | Moturu et al. |
| 2017/0293846 A1 | 10/2017 | Zyglowicz et al. |
| 2019/0209022 A1* | 7/2019 | Sobol .................. A61B 5/0022 |

OTHER PUBLICATIONS

EP19893550.4, "Extended European Search Report", mailed Jun. 29, 2022, 9 pages.
International Application No. PCT/US2019/064630, International Preliminary Report on Patentability mailed on Jun. 17, 2021, 11 pages.
International Application No. PCT/US2019/064630, International Search Report and Written Opinion mailed on Feb. 11, 2020, 12 pages.
Ambrosy et al., The Global Health and Economic Burden of Hospitalizations for Heart Failure: Lessons Learned from Hospitalized Heart Failure Registries, Journal of the American College of Cardiology, vol. 63, No. 12, Apr. 1, 2014, pp. 1123-1133.
Ancoli-Israel et al., The Role of Actigraphy in the Study of Sleep and Circadian Rhythms, Sleep, vol. 26, No. 3, May 1, 2003, pp. 342-392.
Benjamin et al., Heart Disease and Stroke Statistics-2017 Update: A Report from the American Heart Association, Circulation, vol. 135, No. 10, Mar. 7, 2017, pp. e146-e603.
Borazio et al., Towards Benchmarked Sleep Detection with Inertial Wrist-Worn Sensing Units, IEEE International Conference on Healthcare Informatics, Sep. 2014, pp. 125-134.
Chaudry et al., Telemonitoring in Patients with Heart Failure, New England Journal of Medicine, vol. 363, No. 24, Dec. 9, 2010, pp. 2301-2309.
Cornelissen, Cosinor-Based Rhythmometry, Theoretical Biology and Medical Modelling, vol. 11, No. 16, Apr. 11, 2014, 24 pages.
Costa et al., Multiscale Entropy Analysis of Complex Physiologic Time Series, Physical Review Letters, vol. 89, No. 6, Aug. 5, 2002, pp. 068102-1-068102-4.
Desai, Home Monitoring Heart Failure Care Does Not Improve Patient Outcomes: Looking Beyond Telephone-Based Disease Management, Circulation, vol. 125, No. 6, Feb. 14, 2012, pp. 828-836.
Dharmarajan et al., Declining Admission Rates and Thirty-Day Readmission Rates Positively Associated Even Though Patients Grew Sicker Over Time, Health Affairs, vol. 35, No. 7, Jul. 2016, pp. 1294-1302.
Dickstein et al., ESC Guidelines for the Diagnosis and Treatment of Acute and Chronic Heart Failure 2008: The Task Force for the Diagnosis and Treatment of Acute and Chronic Heart Failure 2008 of the European Society of Cardiology, Developed in Collaboration with the Heart Failure Association of the ESC (HFA) and Endorsed by the European Society of Intensive Care Medicine (ESICM),European Heart Journal, vol. 29, No. 19, Oct. 2008, pp. 2388-2442.
Green et al., Development and Evaluation of the Kansas City Cardiomyopathy Questionnaire: A New Health Status Measure for Heart Failure, Journal of the American College of Cardiology, vol. 35, No. 5, Apr. 2000, pp. 1245-1255.

Heidenreich et al., Forecasting the Future of Cardiovascular Disease in the United States: A Policy Statement from the American Heart Association, Circulation, vol. 123, No. 8, Mar. 1, 2011, pp. 933-944.
Jencks et al., Rehospitalizations among Patients in the Medicare Fee-for-Service Program, New England Journal of Medicine, vol. 360, No. 14, Apr. 2, 2009, pp. 1418-1428.
Jones et al., The KCCQ-12: A Short Version of the Kansas City Cardiomyopathy Questionnaire, Circulation: Cardiovascular Quality and Outcomes, vol. 6, No. Suppl_1, 2013.
Koehler et al., Impact of Remote Telemedical Management on Mortality and Hospitalizations in Ambulatory Patients with Chronic Heart Failure: The Telemedical Interventional Monitoring in Heart Failure Study, Circulation, vol. 123, No. 17, May 3, 2011, pp. 1873-1880.
Krumholz et al., Trends in Hospitalizations and Outcomes for Acute Cardiovascular Disease and Stroke, 1999-2011, Circulation, vol. 130, No. 12, Sep. 16, 2014, pp. 966-975.
Loehr et al., Heart Failure Incidence and Survival (From the Atherosclerosis Risk in Communities Study), American Journal of Cardiology, vol. 101, No. 7, Apr. 1, 2008, pp. 1016-1022.
McConnell et al., Feasibility of Obtaining Measures of Lifestyle from a Smartphone App: The MyHeart Counts Cardiovascular Health Study, JAMA Cardiology, vol. 2, No. 1, Jan. 2017, pp. 67-76.
Metra et al., Heart Failure, The Lancet, vol. 390, No. 10106, Oct. 28, 2017, pp. 1981-1995.
Mormont et al., Marked 24-h Rest/Activity Rhythms are Associated with Better Quality of Life, Better Response, and Longer Survival in Patients with Metastatic Colorectal Cancer and Good Performance Status, Clinical Cancer Research, vol. 6, No. 8, Aug. 2000, pp. 3038-3045.
Ong et al., Effectiveness of Remote Patient Monitoring After Discharge of Hospitalized Patients with Heart Failure the Better Effectiveness After Transition-Heart Failure (BEAT-HF) Randomized Clinical Trial, JAMA Internal Medicine, vol. 176, No. 3, Mar. 1, 2016, pp. 310-318.
Osipov et al., Objective Identification and Analysis of Physiological and Behavioral Signs of Schizophrenia, Journal of Mental Health, vol. 24, No. 5, Sep. 3, 2015, pp. 276-282.
Palmius et al., A Multi-Sensor Monitoring System for Objective Mental Health Management in Resource Constrained Environments, Appropriate Healthcare Technologies for Low Resource Settings, Sep. 2014, pp. 1-4.
Palmius et al., Detecting Bipolar Depression from Geographic Location Data, IEEE Transactions on Biomedical Engineering, vol. 64, No. 8, Aug. 2017, pp. 1761-1771.
Reinertsen et al., A Review of Physiological and Behavioral Monitoring with Digital Sensors for Neuropsychiatric Illnesses, Physiological Measurement, vol. 39, No. 5, May 15, 2018, 66 pages.
Reinertsen, Continuous Assessment of Schizophrenia Using Heart Rate and Accelerometer Data, Physiological Measurement, vol. 38, No. 7, Jun. 27, 2017, pp. 1456-1471.
Reinertsen et al., Heart Rate-Based Window Segmentation Improves Accuracy of Classifying Posttraumatic Stress Disorder Using Heart Rate Variability Measures, Physiological Measurement, vol. 38, No. 6, Jun. 2017, pp. 1061-1076.
Shashikumar et al., A Deep Learning Approach to Monitoring and Detecting Atrial Fibrillation using Wearable Technology, IEEE EMBS International Conference on Biomedical & Health Informatics, Feb. 2017, pp. 141-144.
Shaw et al., Mobile Health Devices: Will Patients Actually Use Them?, Journal of the American Medical Informatics Association, vol. 23, No. 3, May 2016, pp. 462-466.
Someren et al., Bright Light Therapy: Improved Sensitivity to Its Effects on Rest-Activity Rhythms in Alzheimer Patients by Application of Nonparametric Methods, Chronobiology International, vol. 16, No. 4, 1999, pp. 505-518.
Speier et al., Evaluating Utility and Compliance in a Patient-Based eHealth Study Using Continuous-Time Heart Rate and Activity Trackers, Journal of the American Medical Informatics Association, vol. 25, No. 10, Oct. 1, 2018, pp. 1386-1391.
Steinhubl et al., The Emerging Field of Mobile Health, Science Translational Medicine, vol. 7, No. 283, 283rv3, Apr. 15, 2015, 12 pages.

(56) References Cited

OTHER PUBLICATIONS

Tang et al., Relationship Between Accelerometer-Measured Activity and Self-Reported or Performance-Based Function in Older Adults with Severe Aortic Stenosis, Current Geriatrics Reports, vol. 4, No. 4, Dec. 2015, pp. 377-384.
Van Der Maaten et al., Visualizing Data Using t-SNE, Journal of Machine Learning Research, vol. 9, Nov. 2008, pp. 2579-2605.
Virkkala, Using Accelerometers as Actigraphs : P587, Journal of Sleep Research, vol. 21, No. 1, 2012, pp. 198-199.
Yingling et al., Adherence with Physical Activity Monitoring Wearable Devices in a Community-Based Population: Observations from the Washington, D.C., Cardiovascular Health and Needs Assessment, Translational Behavioral Medicine, vol. 7, No. 4, Dec. 2017, pp. 719-730.
Zile et al., Transition from Chronic Compensated to Acute Decompensated Heart Failure: Pathophysiological Insights Obtained from Continuous Monitoring of Intracardiac Pressures, Circulation, vol. 118, No. 14, Sep. 30, 2008, pp. 1433-1441.
Zou et al., Regularization and Variable Selection via the Elastic Net, Journal of the Royal Statistical Society, Series B (Statistical Methodology), vol. 67, No. 2, Apr. 2005, pp. 301-320.

\* cited by examiner (a) Actigraphy levels (Subject 1).

(b) Actigraphy levels (Subject 2).

(e) KCCQ scores over time (Subject 1).

(f) KCCQ scores over time (Subject 2).

Table I: Mean absolute error of LOOCV KCCQ estimation models.

| Subject | Num. of KCCQ Scores | Initial KCCQ Score | MAE of Activity Features | MAE of Location Features | MAE of Communication Features | MAE of Combined Features | Std of KCCQ Scores | MAE of Initial KCCQ Model |
|---|---|---|---|---|---|---|---|---|
| 1 | 254 | 95 | 0.43 | 0.90 | 0.91 | 0.44 | 1.97 | 2.12 |
| 2 | 10 | 50 | - | 2.26 | 2.47 | 2.25 | 3.38 | 40.39 |
| 3 | 12 | 13 | 4.93 | - | 4.01 | 3.92 | 4.71 | 4.74 |
| 4 | 46 | 56 | 5.45 | 7.73 | 6.44 | 5.45 | 10.56 | 34.86 |
| 5 | 41 | 71 | 5.46 | 5.44 | 5.68 | 5.49 | 5.93 | 6.61 |
| 6 | 79 | 38 | 7.50 | 12.08 | 7.41 | 7.52* | 20.84 | 17.96 |
| 7 | 23 | 77 | 9.41 | 9.55 | 7.82 | 7.85* | 11.31 | 19.87 |
| 8 | 35 | 19 | - | 12.32 | 8.82 | 7.99* | 9.04 | 6.10 |
| 9 | 72 | 13 | 8.22 | 8.31 | - | 8.33 | 10.21 | 19.31 |
| 10 | 13 | 33 | - | - | 10.90 | - | 15.47 | 13.32 |
| AVG | 59 | 45 | 5.71 | 7.40 | 6.05 | 5.43 | 9.34 | 16.53 |

FIG. 6

PASSIVE DATA COLLECTION AND USE OF MACHINE-LEARNING MODELS FOR EVENT PREDICTION

PRIORITY CLAIM

This application claims priority to U.S. Provisional Application No. 62/777,029 filed on Dec. 7, 2018, the entirety of which is incorporated herein by reference for all purposes.

STATEMENT REGARDING FEDERALLY SPONSORED RESEARCH OR DEVELOPMENT

This invention was made with government support under Grant No. HL127251 awarded by the National Institutes of Health and 1636933 awarded by the National Science Foundation. The government has certain rights in the invention.

FIELD OF THE INVENTION

Techniques described herein relate to passive monitoring of sensor data for processing by machine-learning models to generate event predictions. More specifically, an electronic device or wearable smart device may monitor the output of various sensors to collect data related to a person's activity level, location changes, and communications and may use this information as input to a trained machine-learning model to predict a likelihood of an event (e.g., heart failure).

BACKGROUND OF THE INVENTION

Heart failure is characterized by structural or functional cardiac abnormalities that lead to elevated intracardiac pressures and/or reduced cardiac output. Twenty-six million people worldwide live with heart failure. Mortality remains unacceptably high. For example, in one study, the 30-day, 1-year, and 5-year case fatality rates after hospitalization for heart failure were 10.4%, 22%, and 42.3%, respectively. Heart failure is one of the most common causes of hospitalization and readmission. In 2011, the heart failure hospitalization rate in the USA was 18 per 1000 for those over age 64, making heart failure among the leading causes of hospitalization in this age group.

Heart-failure readmissions are perceived as a correctable source of poor quality of care and excessive medical spending. The cost of medical care and productivity losses in 2012 due to heart failure were estimated to be $31 billion, a figure estimated to rise to $53 billion by 2030. Since passage of the Affordable Care Act in 2010 in the United States, providers have been financially penalized for higher than average heart-failure readmission rates, and readmissions have declined from 17.2 to 16.1 per 100 hospital discharges. However, one-fifth of those who are hospitalized with heart failure are still readmitted within 30 days.

Interventions to reduce heart failure readmissions have only achieved very limited success and require relatively high numbers of trained staff to implement the programs. Recent advances in telecommunication technologies provide new opportunities to remotely monitor and manage subjects with heart failure as an adjunct to direct care. However, there are conflicting reports as to whether telemedicine programs decrease morbidity and mortality in heart failure. Factors associated with readmission that were assessed in these studies included blood pressure, body weight, heart rate and symptoms, none of which have been shown to be good predictors of acute decompensation, or effective when coupled with an intervention.

However, worsening symptoms of heart failure such as lower extremity edema, shortness of breath, and fatigue may be good predictors of potential readmission and may be associated with alterations in locomotor activity and other behavioral patterns. Changes in locomotor activity and behavioral patterns may be detectable through sensors integrated into a variety of smart computing devices. Accelerometry and location data from electronic devices and wearable devices may be gathered in the context of everyday living. The detected changes may be used to predict the risk of experiencing a health event such as heart failure.

BRIEF DESCRIPTION OF THE DRAWINGS

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure. The present disclosure is described in conjunction with the appended figures:

FIG. 6 is a data table illustrating error in estimation of KCCQ scores according to some embodiments.

Figure 1:
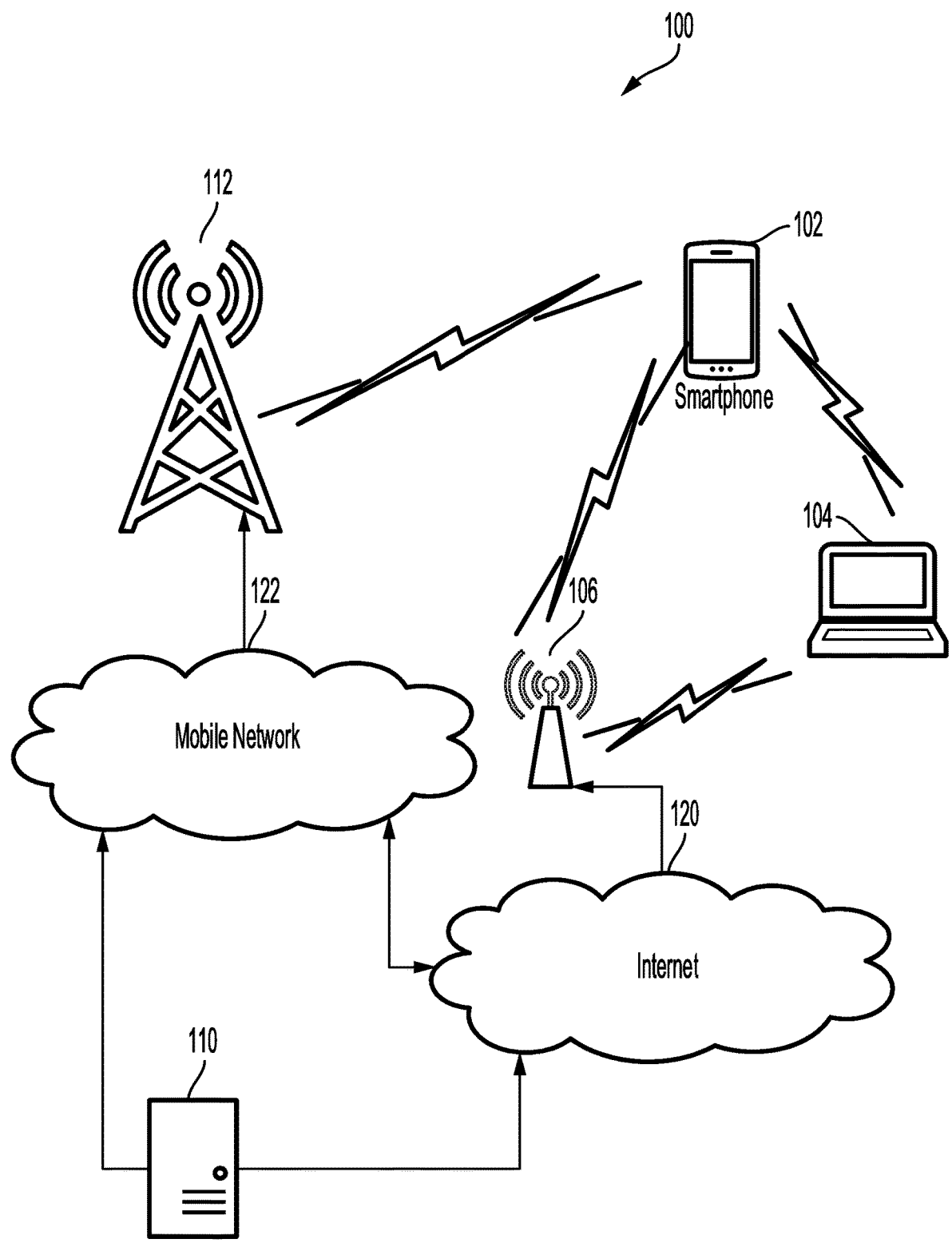
FIG. 1 is a block diagram of an exemplary communication system suitable for processing sensor data by machine-learning models to generate event predictions, according to various embodiments.

Additional details may be found within the attached appendix. In the figures, similar backings and/or features may have the same reference label. Where the reference label is used in the specification, the description is applicable to any one of the similar backings having the same reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In some embodiments, an electronic device can passively collect (e.g., via an installed application) activity and location data. This data can be processed (e.g., via execution of the application) to generate a result that is predictive as to whether a user is experiencing an event (e.g., heart failure). In some instances, the result corresponds to an inferred quality of life or assessment of one or more physiological systems of the user, which may be predictive of a degree of the event. The result can correspond to a subject-identified rating on a self-reported clinical scale, In some instances, the result may instead of or additionally be predictive of a state of another disease or disorder, such as an illness severity in schizophrenia, depression, chronic pulmonary disorder, post-traumatic stress disorder or bipolar disorder.

The processing of the collected data may extend beyond the use of simple and/or multiple linear regression models. More sophisticated time series analyses or statistical learning techniques could identify predictive features that would not be detected via simple characteristics. Estimation of outcomes such as the inferred quality of life based on passively monitored data gathered via electronic device has not been previously reported. Such an approach may improve monitoring efforts and further understanding of the physiological and behavioral determinants of events and factors associated such events (e.g., heart failure-related quality of life) and predictors of clinical decompensation.

Various embodiments may construct subject-specific or subject-type models to estimate KCCQ scores (a validated survey to assess quality of life, predict readmissions and mortality in subjects) based on passively monitored sensor data. For example, a device may passively collect sensor data over a period of time, and input (e.g., that corresponds to a quality-of-life score) may be collected at one or more time points within the period of time (or just after the period of time). The machine-learning model may be trained to learn parameters that can be used to transform sensor data to the quality-of-life score. In some instances, the output of the machine-learning model includes or is processed to generate (for example) a categorical value (e.g., predicting whether sensor data indicates that there is a high, medium or low probability that the user is experiencing heart failure) or a numeric value on another scale. In one instance, an output is processed to assign an instance to a cluster. The output value can determine a cluster to which the output instance should be assigned. For example, a first instance, based on the its corresponding output value, can be assigned to a cluster that indicates a high probability of heart failure (KCCQ≤25). In another example, a second instance, based on its corresponding output value, can be assigned to a cluster that indicates a moderate probability of heart failure (KCCQ≤25).

In some instances, techniques are provided to infer events (e.g., heart-failure incidences) only based on passively data collected from via electronic device. With the rapid growth of personal hand-held communication technology, electronic devices have become an essential component of our daily life. Data collected from these devices can provide a high-compliance signal which provides valuable insight into a subject's daily behaviors and health status. Physical activity, location, and communication data may all be affected by changes in health status for subjects, and these data gathered via an electronic device can be used to assess subject quality of life.

Physical activity data can be used to infer circadian rhythm, activity-rest schedules, and/or disruptions (such as awakenings during night) of a subject. For instance, users may be less active than normal or have disrupted schedules (particularly at night) before event incidences (e.g., associated with low KCCQ scores). The physical activity data can be collected (for example) using an accelerometer or a gyroscope sensor, a GPS receiver (to continuously or periodically detect a user's location to use for movement calculations), etc.

Location data may indicate if a subject is disinclined or unable to leave the house. In some instances, the location data indicates if the subject is disinclined or unable to continue a normal routine such as going to work, the shops, the gym, or other habitual locations. Such indications may further or alternatively be predictive of an event such as heart failure. The location data can be collected (e.g., using a GPS, dead-reckoning techniques, together with accelerometer output, or software applications providing location information). To create a location data entry, the subject may be required to move a minimum distance (e.g. at least 100 meters) after some time (e.g. 5 minutes) since the last location data update. A random offset may be added to each location data entry to protect privacy. Home and work locations can be inferred from the most frequently visited locations (or locus or points). Changes in proportions of times at these locations, and at specific times of the data, can be predictive of improvements or worsening of conditions.

Communication data provides information about a subject's communication interaction, particularly with a given subgroup of contacts. Thus, the communication data can include or can be based on data pertaining to incoming and/or outgoing calls or text messages. During health changes, communication patterns of the subject may shift or change. For example, a user may communicate with different individuals, change the amount of time they spend communicating with specific entities, and/or be less likely to initiate calls or to send text messages. Further, calls and/or texts (e.g., on average) may be shorter, and/or calls and/or texts may be sent to fewer unique people. Moreover, word frequencies and complexities of grammar in text messages and phone calls may change to reflect worsening cognition. In some instances, key words/phrases detected from the text messages and/or phone calls indicates a severity of the illnesses. Estimations of severity or probability of readmission corresponding to events (e.g., heart failure) may be even more accurate when accounting for two or more types of data (physical-activity data, location data and/or communication data).

Thus, in some instances, features extracted from the three domains (physical activity, location and communication) can be used to build clinically useful models. The machine-learning model can be configured to output a KCCQ estimate based on sensor data from the three domains. The estimated KCCQ score can then be transformed into categorical values predictive of event risk by comparing each score to one or more threshold (e.g., whether a given score is less than 25 or not).

In various embodiments, a software application operating on the electronic device of a user, may access location, activity, battery usage and communication data collected at the device. The communication data can include a de-identified list of contacts with which the device communicated (via text and/or call), word types or key phrases used in individual text messages, lengths of individual calls and/or text messages. The application can further access environmental data associated with a device location and/or inputs received at the device (e.g., temperature, humidity, air pollution levels, traffic conditions, etc.). In some instances, the application further accesses data corresponding to a self-reported mood and/or responses to one or more questions on a questionnaire such as the KCCQ. Data may be collected up to several samples per second. The software application may upload data to a remote server every few hours for storage (and further analysis) when the electronic device has sufficient battery and internet connection. This store and-forward method may enable near real-time monitoring and data collection despite network and application outages.

The collected and stored data may be passed as an input to a machine learning model to produce a result predicting an estimated risk of event (e.g., heart failure). The result can be presented either on the phone or on a remote server. Subject-specific models may be trained with a user's initial reported KCCQ scores during the period when most users are committed to health management and before natural attrition of compliance begins. Subject-type models may use clustering techniques to classify a data set as corresponding to one of a number of groups (e.g., each being associated with a different level of risk of heart failure).

In some embodiments, a result of a machine-learning model execution can be processed to determine whether an alert condition is satisfied. For example, an alert condition may indicate that an alert is to be presented (e.g., via a visual or audio stimulus) when a result is above a predefined threshold. Satisfaction of the alert condition may also trigger a change in a device's operation. For example, a frequency of passive monitoring of sensor outputs may be changed and/or a frequency at which a sensor collects measurements may be changed. In addition to or instead of modifying sampling frequency, the electronic device may also alter the scope of data being collected. For example, initial data collection may include only a few types of location, communication, and movement data. However, in response to determining that the event corresponds to a high-risk event (e.g., the user is at high risk for heart failure), the electronic device may examine a larger pool of sensor output or increase the sampling rate. For example, in addition to counting text messages from a single messaging application, the electronic device may begin counting or observing the volume of messages sent through additional messaging applications. The location data may be toggled to refine the granularity of what is considered to be a base location, in order to obtain data about the frequency and range of "small trips" made by the user. In this way, the prediction of events by the trained model may provide feedback to influence which data is collected by the device and/or to adjust a granularity, scope, or sampling spatial and temporal resolution of data to be collected.

Some or all of the data collected or generated by the electronic device may be transmitted to another user device (e.g., cloud computer or other user device). In some instances, the data is conditionally transmitted (e.g., when an alert condition is specified).

The other user device can correspond to a device of an identified caregiver, physician, or third party monitoring the user's health record. An identifier associated with the other device (e.g., phone number or email address) may have been previously provided via input in response to a prompt for such information. The transmission may (for example) cause an alert to be presented at a other device, in which the alert indicates recommendations for scheduling an appointment for the user, contacting the user, scheduling a call with the user, or updating the plan of treatment for the user. In some implementations, the notification may trigger processing to initiate readmission procedures at a hospital and/or processing to prepare accommodations and a plan of treatment for the user.

Using the embodiment methods described herein, predictive and classification models may be built by extracting features from passively collected data sources. These trained models may estimate KCCQ scores, a measure of quality of life in subjects experiencing certain medical conditions (e.g., heart failure), for individuals with high accuracy. A classification model may be trained to identify significant changes in severity which would require an intervention or reassessment of treatment. This framework may be applied to a large population with very low cost, high compliance, and a rapid response rate compared to existing approaches. The various embodiments may thus enable the early prediction of events and may enable users and treating physicians to prepare for potential incidents. Early detection and preparation may reduce occurrences of events, including fatal cases of heart failure.

Various embodiments may be implemented within a variety of communications systems 100, an example of which is illustrated in FIG. 1. A mobile network 122 may include a plurality of cellular base stations (e.g., a first base station 112). The mobile network 122 may also be referred to by those of skill in the art as access networks, radio access networks, base station subsystems (BSSs), Universal Mobile Telecommunications Systems (UMTS) Terrestrial Radio Access Networks (UTRANs), etc. The network 122 may use the same or different wireless interface technologies and/or physical layers. In an embodiment, the base stations 112 are controlled by one or more base station controllers (BSCs). Alternate network configurations may also be used and the embodiments are not limited to the configuration illustrated.

A first computing device 102 may be in communications with the mobile network 122 through a cellular connection to the first base station 112. The first base station 112 may be in communications with the mobile network 122 over a wired connection. The cellular connection may be made through two-way wireless communications links, such as Global System for Mobile Communications (GSM), UMTS (e.g., Long Term Evolution (LTE)), Frequency Division Multiple Access (FDMA), Time Division Multiple Access (TDMA), Code Division Multiple Access (CDMA) (e.g., CDMA 1100 1x), WCDMA, Personal Communications (PCS), Third Generation (3G), Fourth Generation (4G), Fifth Generation (5G), or other mobile communications technologies. In various embodiments, the computing device 102 may access network 122 after camping on cells managed by the base station 112.

In some embodiments, the computing device 102 may establish a wireless connection with a wireless access point 106, such as over a wireless local area network (WLAN) connection (e.g., a Wi-Fi connection). In some embodiments, the computing device 102 may establish a wireless connection (e.g., a personal area network connection, such as a Bluetooth connection) and/or wired connection (e.g., a USB connection) with a second computing device 104. The second computing device 104 may be configured to establish a wireless connection with the wireless access point 106, such as over a WLAN connection (e.g., a Wi-Fi connection). The wireless access point 106 may be configured to connect to the Internet 120 or another network over a wired connection, such as via one or more modem and router. Incoming and outgoing communications may be routed across the Internet 120 to/from the computing device 102 via the wireless and/or wired connections.

In some embodiments, the computing device 102 may utilize wireless and/or wired connections to transmit and receive information from a remote server 110. While FIG. 1 shows one mobile device connected to a second computing device 104, the various embodiments are equally applicable to multiple mobile devices connected to a remote server or the cloud.

Figure 2A:
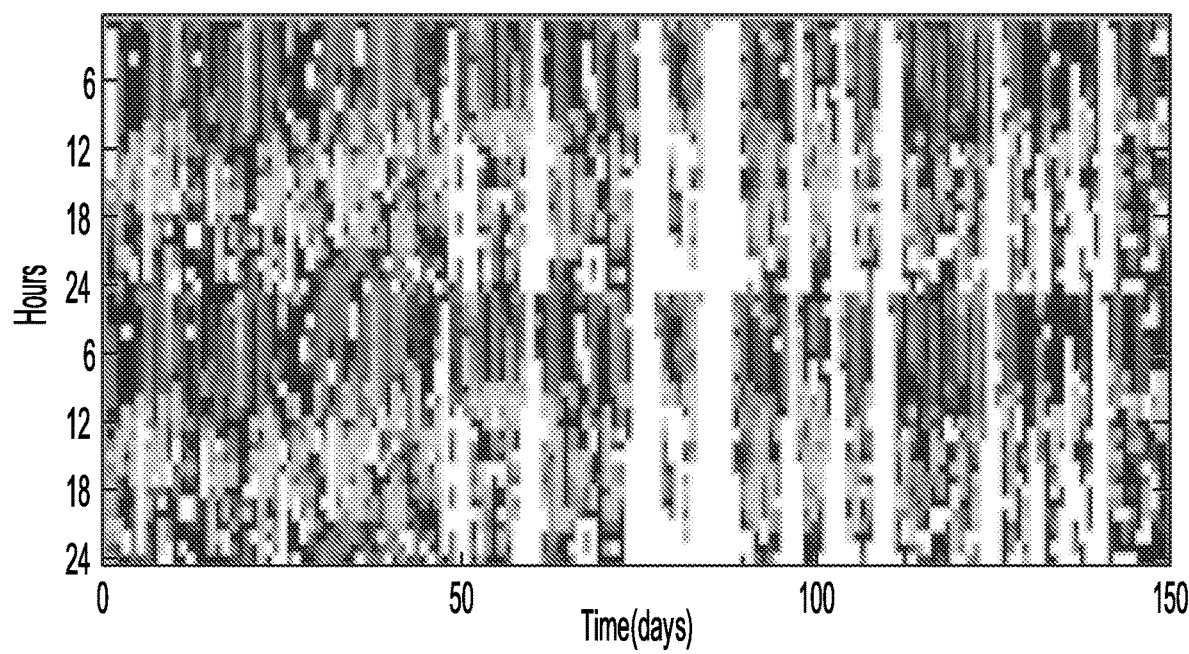
FIG. 2A is a graph illustrating actigraphy levels in a subject.
Figure 2B:
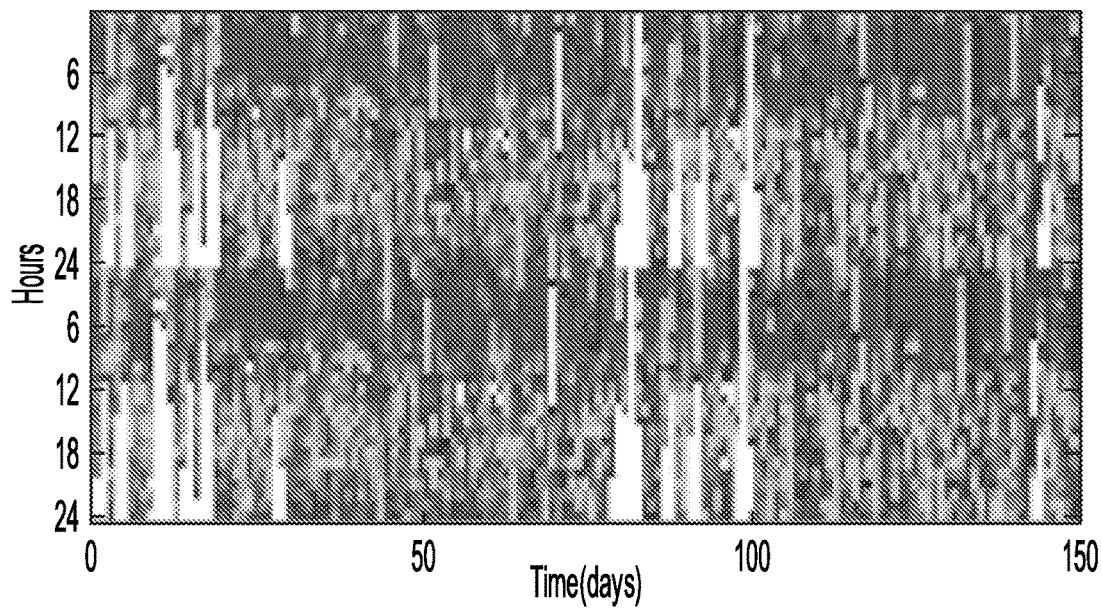
FIG. 2B is a graph illustrating actigraphy levels in a subject.

FIGS. 2A and 2B shows example graphs that illustrate actigraphy levels of two subjects. In particular, FIG. 2A shows a graph indicating actigraphy levels of a first subject (Subject 1) associated with low KCCQ scores. FIG. 2B shows another graph indicating actigraphy levels of a second subject (Subject 2) associated with higher KCCQ scores. Actigraphy levels may refer to metrics that correspond to recorded activity levels of a subject. The actigraphy levels may indicate an amount of rest (e.g., sleep) taken by the subject. Higher actigraphy levels may represent more movement. The actigraphy levels can be calculated based on movement (e.g., physical activity) data collected by the electronic device's 3D accelerometer. Accelerometry may be measured in the x, y, z axes and sampled at 5 Hz. FIGS. 2A-2B may each indicate a "double plot" that shows physical activity levels measured using accelerometry over a specified period (e.g., 150 days). Each column can be created by stacking two consecutive days of data. For example, the first column may show activity levels on day 1-2, the second column may show activity levels on day 2-3, etc. White regions in the plot may indicate a lack of activity data (e.g., if the subject chose to not share data during that time or if the electronic device ran out of battery). Darker colors in regions of the graphs may indicate lower activity and white indicates missing data (when the phone is off). A horizontal black stretch in FIG. 2B between hours 2 and 12 may indicate that Subject 2 typically sleeps during this interval. The lack of a stable block of low movement (black) in FIG. 2A may indicate that Subject 1 is associated with less regular and/or less stable sleeping patterns. Raw 3D-accelerometer data may be converted to activity counts. Activity counts may refer to an output format common to actigraphy devices. To convert the raw data into activity counts, the 3D-accelerometer data may be summarized over 30-second epochs or time intervals (for example). In some instances, actigraphy levels are calculated using a 0.25-11 Hz passband to eliminate extremely slow or fast movements. The maximum values inside 1-second windows can be summed for each 30-second epoch of data for visualization and graph-plotting. These summations can be scaled to obtain activity counts for each epoch. The conversion from the raw data to the activity counts can compress information, reduce required memory for storing data, and eliminate artifacts and noise in the raw data.

The actigraphy data (e.g., the actigraphy levels illustrated in FIGS. 2A and 2B) can be processed to identify multiple features related to subjects' activity and/or circadian rhythm. Rest activity rhythms may be assessed using (for example) Interdaily Stability, Intradaily Variability, Most Active 10 Hours and/or Least Active 5 Hours. Interdaily stability quantifies invariability between days and can be calculated. Cosinor rhythmometry may also be monitored. To extract cosinor rhythmometry features, a cosine model of a predetermined form may be fit to the data. Multiscale entropy may be calculated to quantify irregularity or unpredictability of behavior over multiple timescales. Changes in entropy can be due to sleep, skittish behavior, sedentary activity, or a lack of a structured daily routine. Actigraphy time series may be coarse-grained by averaging the data points within non-overlapping windows. The first 20 scales of multiscale entropy can be calculated by varying the window size from 1 to 20. For each coarse-grained time series, sample entropy may be calculated.

Figure 3A:
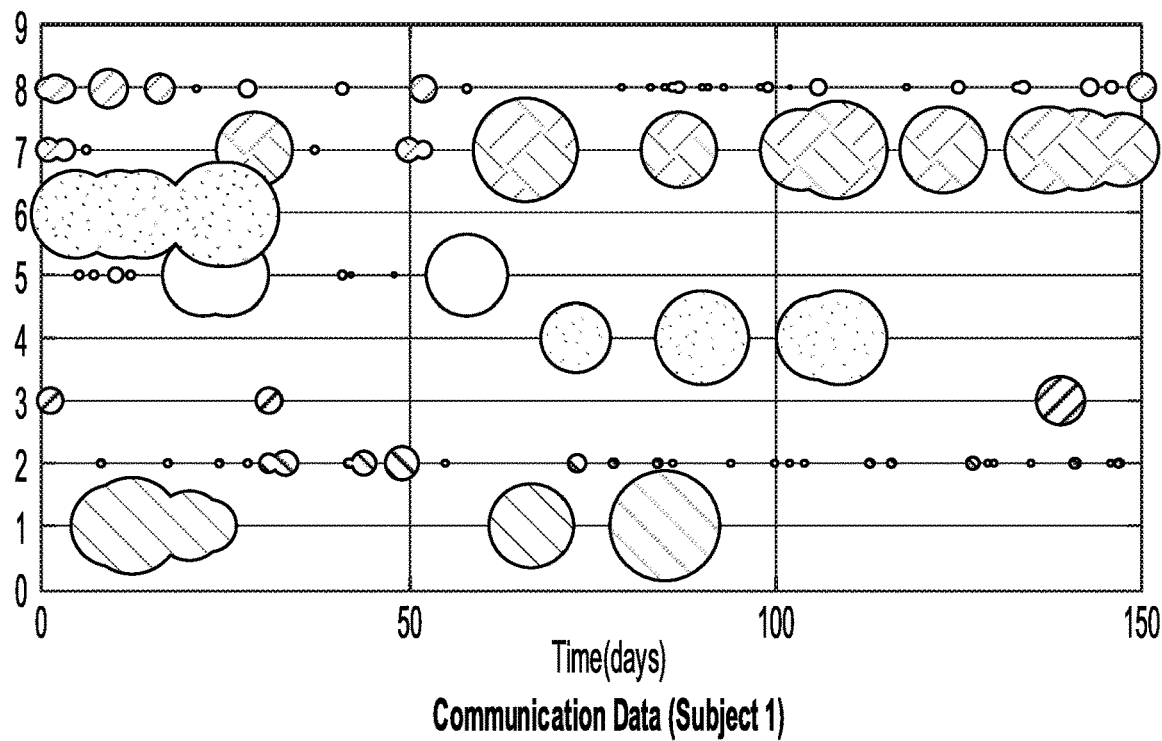
FIGS. 3A-3B show graphs illustrating communication data corresponding to two subjects.
Figure 3B:
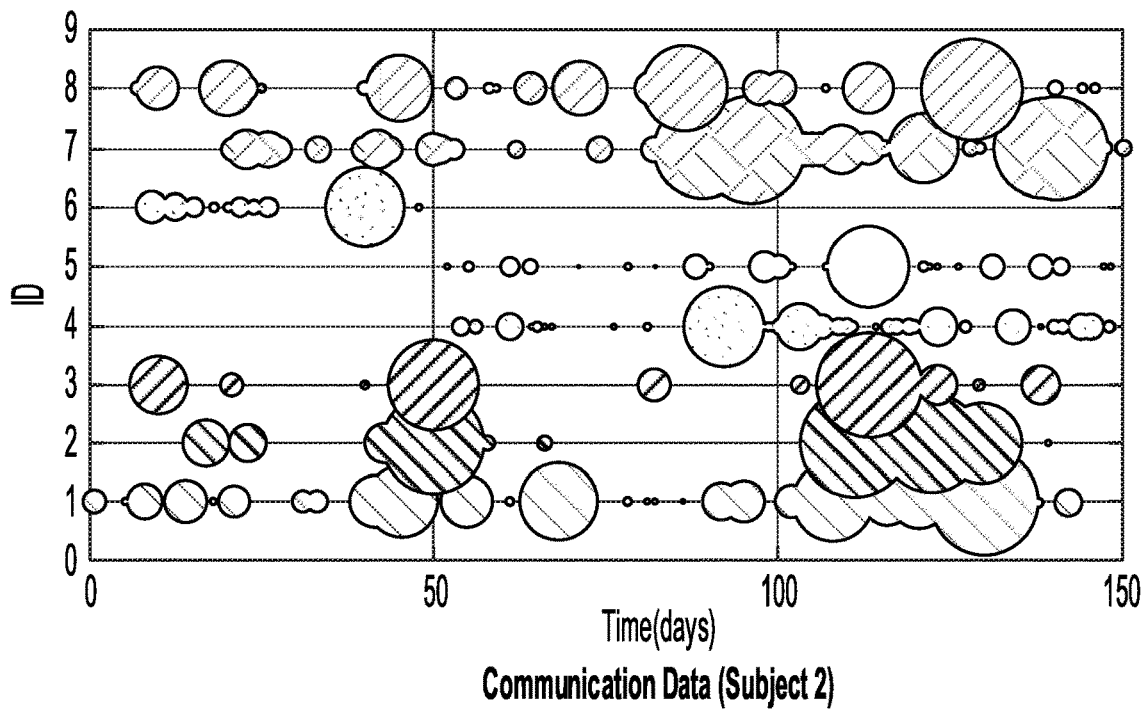

FIGS. 3A and 3B show graphs that illustrate communication data collected via electronic phones of the same two subjects. FIG. 3A shows a graph illustrating communication data for Subject 1, and FIG. 3B shows a graph illustrating communication data for Subject 2. To collect this data, an application executing on a mobile device may access call and/or message data. The duration of each call can be detected, and a unique identifier can be assigned to each number with which the call is associated. Each of FIGS. 3A and 3B shows an x-axis that indicates time and a y-axis that indicates identifiers corresponding to individuals that communicated with the subjects. Size of a circle radius illustrated in the graphs of FIGS. 3A and 3B may be proportional to the call duration. unique individuals are encoded by color. For example, the depicted graph of FIGS. 3B may indicate that Subject 2 placed a higher number of longer calls within days 101-150 as compared to days 1-50 or 51-100.

The communication data may be processed to generate one or more communication statistics for a subject in correspondence to a time interval. Exemplary statistics include a total number of calls; mean duration of calls; standard deviation (std) of duration of calls; mean duration without any calls: In addition to call duration; and/or time interval between each call.

Figure 4A:
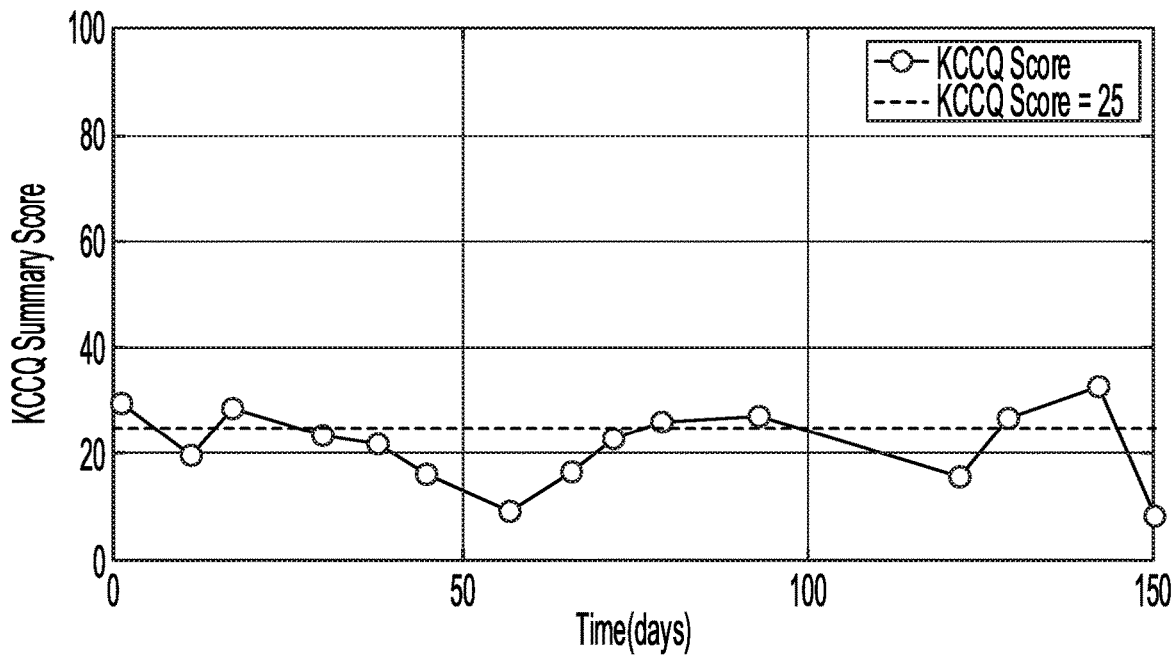
FIG. 4A is a graph illustrating the Kansas City Cardiomyopathy Questionnaire (KCCQ) scores in a subject.
Figure 4B:
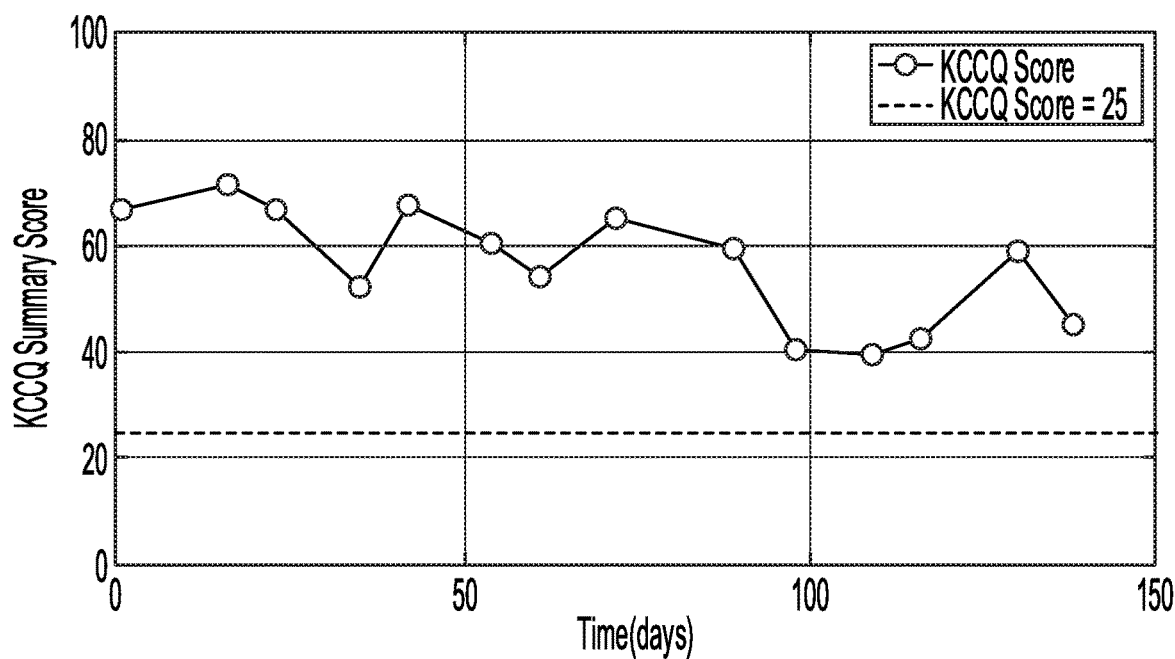
FIG. 4B is a graph illustrating KCCQ scores in a subject.

FIGS. 4A and 4B show graphs illustrating KCCQ scores corresponding to two subjects. FIG. 4A shows a graph indicating KCCQ scores corresponding to Subject 1, and FIG. 4B shows a graph indicating KCCQ scores corresponding to Subject 2. The KCCQ scores can be calculated based on values corresponding to various data fields. In some instances, the KCCQ scores can be calculated based on user input. For example, the scores can represent the KCCQ-12 summary scores. The KCCQ score may quantify physical function, symptoms, social function, self-efficacy and knowledge, and quality of life. A higher score may indicate better health status relative to a lower score. KCCQ scores that are below 25 may indicate a high probability of heart failure. The data shown in FIGS. 4A and 4B may indicate that the probability of heart failure is higher for Subject 1 as compared to Subject 2.

Figure 5:
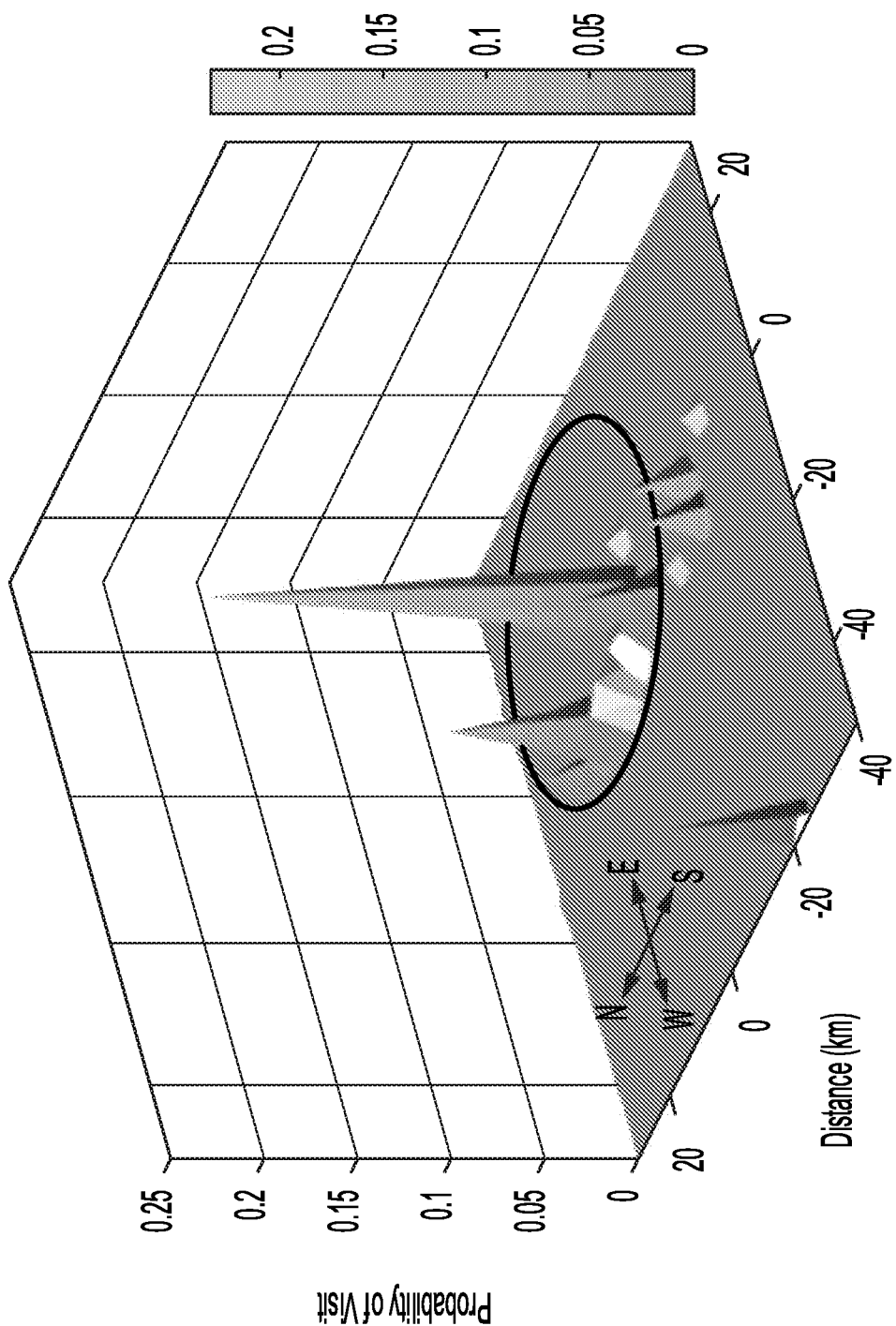
FIG. 5 is a graph illustrating a location probability map for a subject.

FIG. 5 is a graph illustrating a location-change probability map for a subject. The location-change probability map can be determined based on location data collected by a software application operating on electronic devices associated with the subject. The graph may include multiple peaks, in which each peak may indicate a location that the user may visit. The location can be calculated based on a distance from an original location. Increasing peak height, as well as a redundant green-to-light gradient coloring of the peak, can represent the probability of visiting an area. Areas south and west from the origin are represented as negative distances.

A red circle illustrated in the graph is the boundary of "zone-1", which may refer to an area proximate to the most frequently visited location. In some instances, the red circle includes a radius (20 km in this case) that indicate distance from most frequently visited location.

Severe heart failure causes discomfort and can hinder physical activity, which could lead to the subject staying at home more, or altering routine behaviors. Location data may be extracted from the location-change probability map to capture these changes. Location data may include: percentage of time at "home" location. Using all location data from each subject, the "home" location may be defined as the most frequently visited location. The percentage of time spent at "home" may be calculated. A "home" region may be explicitly defined by a user or inferred as corresponding to an area at which an electronic device is most frequently located (across all time or for a particular period of time, such as during night hours). Percentage of time at second most frequent location as well as a percentage of time spent in "zone 1 or "zone 2" may also be calculated as location data. Other location data may include the number of visits to each zone, total distance travelled; and Haversine distances between all locations to the "home" location were summed. The Haversine distance may refer to the shortest distance between two coordinates over the surface of the Earth. Other distances could be used which account for the shortest distance by foot, public transport, car based on the transport most often used by the subject.

Dates of all KCCQ data from each subject were determined. The date can be identified as the date on which input was received that was processed to generate a given score. Passively collected data (or statistics or features generated based thereupon) collected during a window leading up to each KCCQ-score data can be identified and associated with the score. Using a set of associated data elements (each of which includes a KCCQ score and some representation of passively collected data), a machine-learning model can then be trained to transform passively collected data (and/or corresponding statistics or features) into estimated KCCQ scores.

A machine-learning model can be personalized and associated with an individual subject and/or associated with a group of subjects. In some instances, a machine-learning model is trained using training data from one or more subjects other than a subject for which it is subsequently used. In some instances, a machine-learning model is used in association with a subject despite the subject not being associated with training data used to train the machine-learning model.

A machine-learning model can include (for example) a generalized linear model. Covariates may be physical activity and location features, and the outcome may be the KCCQ summary score. Since the KCCQ summary score may be normalized to a proportion ranging from 0-1, a generalized linear model (GLM) with a binomial distribution and logit link may be used.

The machine-learning model may use an elastic net regularization that linearly combines penalties and acts as a feature selection method. Compared to the least absolute shrinkage and selection operator (LASSO) method, the elastic net selects more variables before saturating, and tends to include more variables from a group of correlated variables. This results in decreased bias and improved classification performance.

The machine-learning model may alternatively or additionally use a K-Nearest Neighbors classification approach. KCCQ scores can be classified into one or more groups based on comparisons to one or more thresholds. For example, KCCQ scores may be classified into groups corresponding to scores above 25 or scores less than or equal to 25. Features or statistics derived from associated passively monitored data can then be used to define clusters for each group. Thus, when new features or statistics are received, it may be assigned to one of the clusters (e.g., using cosine distance and a predefined number of nearest neighbors).

FIG. 6 is a data table illustrating mean average error (MAE) in estimation of KCCQ scores. The error was calculated using leave-one-out cross validation. More specifically, one time window of data was not used to train the machine-learning model and was instead used as a test data set. This process was repeated—each time holding back a different window from training to use it for testing. The machine-learning model was further independently trained using different types of data. In a first instance, the machine-learning model was configured to use only activity features as input. In a second instance, the machine-learning model was configured to used only location features as input. In a third instance, the machine-learning model was configured to use only communication features as input. In a fourth instance, the machine-learning model was configured to use combined features (activity, location and communication features) as input.

As shown in the table of FIG. 6, which individual type of features was associated with the lowest error varied across subjects. For example, activity features were associated with lower errors than location or communication features for Subject 1, but communication features were associated with lower errors than activity or location features for Subject 7. The error was generally the lowest in the fourth instance—when activity, location and communication features were all used as input by the machine-learning model. For example, the cross-subject average MAE using this approach was 5.43%, while the cross-subject average MAE associated with models using only a single type of feature ranged from 5.71% to 7.40%. Further, the MAE for individual subjects did not exceed 8% for any individual subject when a combination of features was used. Thus, this approach may provide an accurate way of monitoring for heart failure, and the passive data collection can increase the frequency at which assessments can be performed.

Figure 7A:
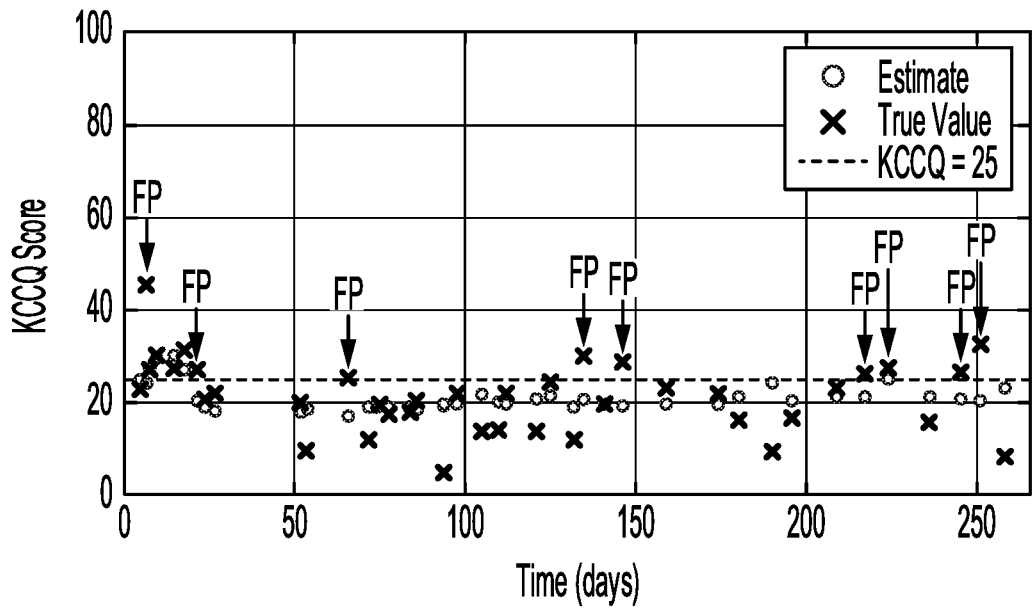
FIG. 7A is a graph illustrating actual KCCQ summary scores and estimated KCCQ scores according to some embodiments.

FIG. 7A is a graph illustrating actual KCCQ summary scores and KCCQ scores estimated according to the various embodiments. This graph pertains to a single subject. The graph shows the KCCQ scores estimated using a generalized linear model trained using the subject's data (red stars) and the actual KCCQ scores (blue x's). The estimated data corresponds to use of the generalized linear model trained only using activity features (not location or communication features). It will be appreciated that the estimated scores can be used to then estimate classifications or group assignments (e.g., corresponding to various likelihoods of experiencing heart failure). The classification or group assignment can be performed by identifying within which of multiple ranges (defined by one or more predefined threshold) an estimated score falls. In this instance, two groups are defined based on whether scores are above or below 25. The graph identifies false positives—which occurred when an actual KCCQ score exceed a classification threshold (which is set here to 25) but when the estimated KCCQ score did not exceed the threshold. In this data set, no false negatives occurred.

The red line indicates the limit (KCCQ score=25) below which subjects are classified as most severe and is independently associated with increased long-term mortality and readmission for HF. Movements below this threshold may be used to trigger interventions. False Positives (FPs) are indicated by an arrow and the abbreviation 'FP', where the machine-learning model predicts a equal to or below 25 and the actual (Self-reported) value is above 25. Note there are no False Negatives (missed events where the subject drops below KCCQ=25, but the machine-learning model predicts the subject above 25).

Figure 7B:
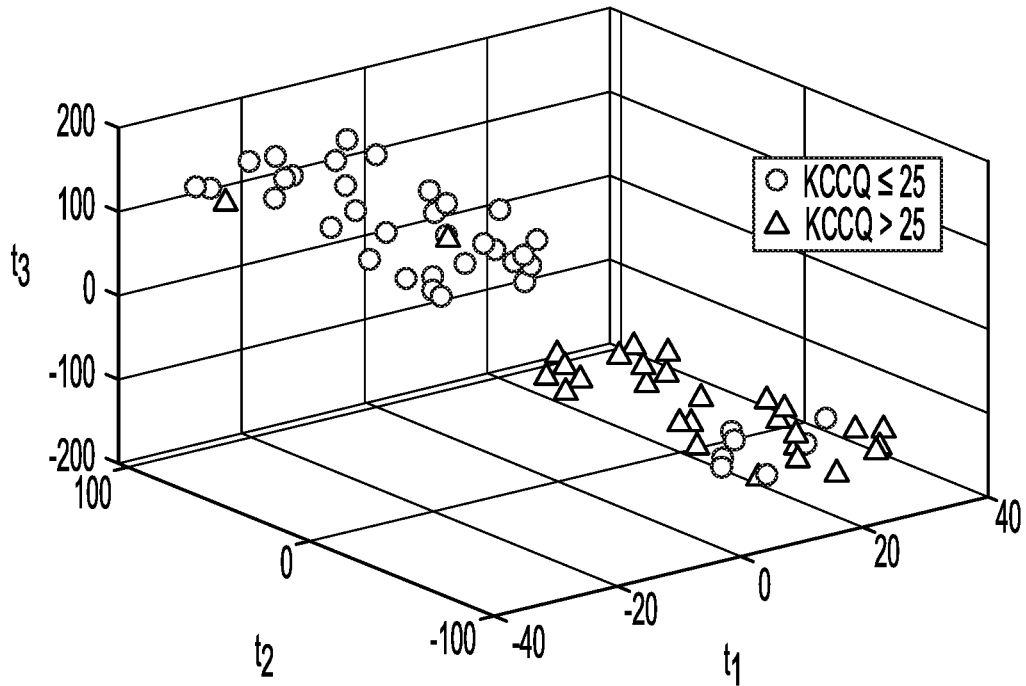
FIG. 7B is a graph illustrating clustering of KCCQ scores into risk groups.

FIG. 7B is a graph illustrating clustering of KCCQ scores into risk groups. The symbols represent whether the actual KCCQ scores were above 25 (triangles) or less than or equal to 25 (circles). The coordinates of each data point identify values along three arbitrary dimensions identified using t-Distributed Stochastic Neighbor Embedding on communication features for two subjects. Using data from these two subjects (Subject 1 and Subject 8 from Table I), five-fold cross validation of the K-NN classification approach may be performed. Out-of-sample classification accuracy for these two subjects (1 and 8) were 0:78 and 0:88 respectively. Repeating the same analysis with location features resulted in respective classification accuracies of 0:65 and 0:73.

Figure 8:
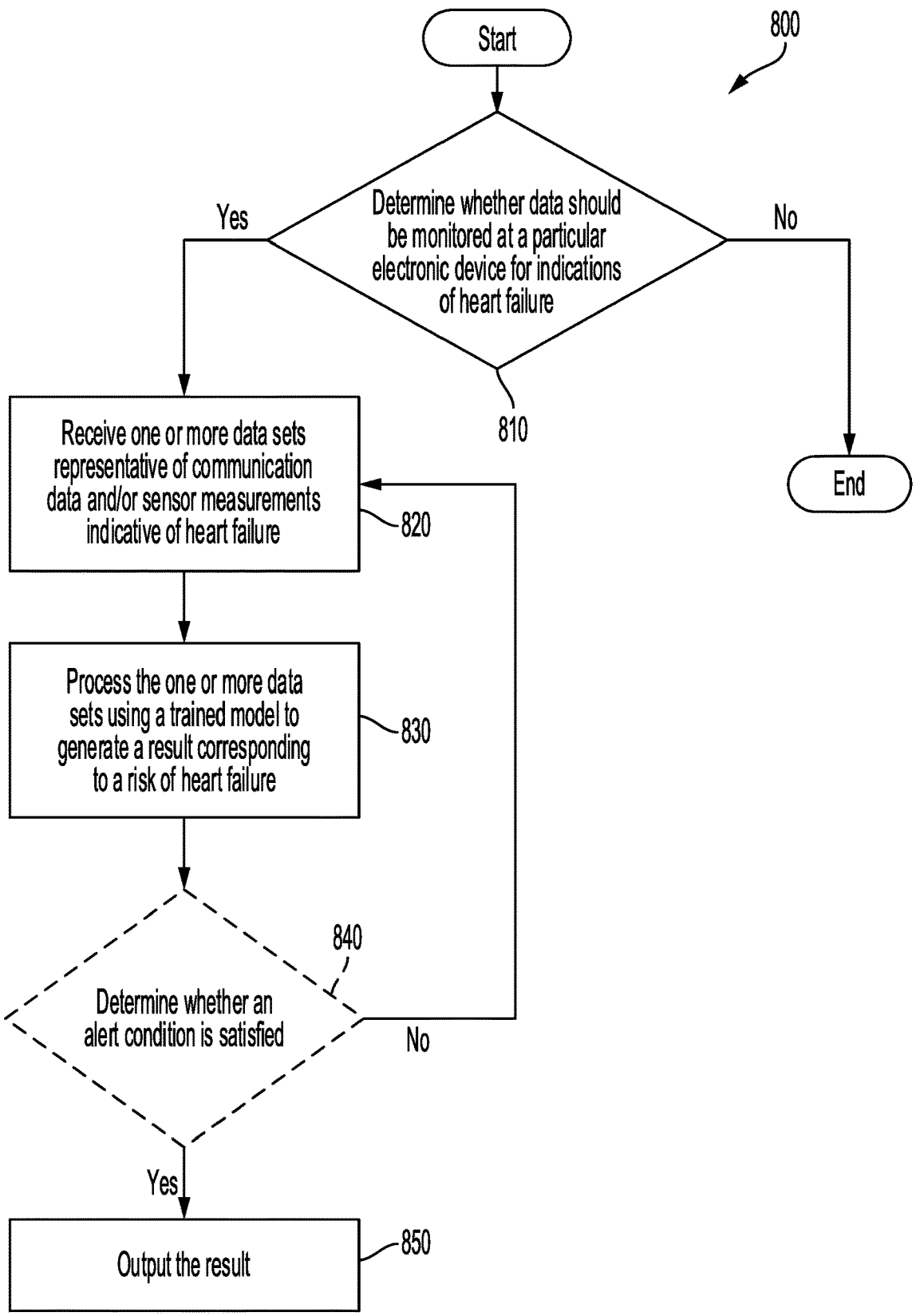
FIG. 8 is a process flow diagram of an embodiment method for monitoring sensor output of an electronic device for processing by machine-learning models to generate event predictions.

FIG. 8 illustrates a process 800 for monitoring sensor output of an electronic device to produce an estimate of heart failure in accordance with an embodiment of the invention. Process 800 may be initiated (for example) by a particular electronic device (e.g., computing device 102) receiving an indication (e.g., from server 110) to begin passive collection of data output from one or more sensors of the particular electronic device. These sensors may include one or more accelerometers, magnetometers, microphones, GPS receivers, transceivers and the like. In some instances, process 800 may be continuously or repeatedly (e.g., regularly) performed.

At block 810, it is determined whether data is to be monitored at the particular electronic device for predictions of heart failure. The determination can include determining whether a monitoring condition is satisfied. The monitoring condition can be configured to be satisfied (for example) when an instruction is received from a particular device, a particular type of device or user input to begin monitoring. The instruction may be detected by an application installed on the electronic device. The monitoring condition can be further or alternatively be configured to be satisfied when it is detected that a current time matches a predefined time to initiate monitoring and/or that at least a predefined amount of time has passed since a previous monitoring event.

If it is determined that data should not be monitored, process 800 may at least temporarily end. It will be appreciated that process 800 may then be immediately or subsequently reinitiated.

If it is determined that data is to be monitored, process 800 continues to block 820 at which one or more data sets representative of communication data and/or sensor measurements are received. The one or more inputs and/or sensor measurements may have been collected at the particular electronic device. In some instances, a processor of the particular electronic device may communicate to a storage memory that sensor output and/or communication data should be stored for a period of time specified in the indication or by the software application, and block 820 can include retrieving the sensor output and/or communication data from storage. In some instances, block 820 includes directly receiving data from one or more sensors and/or one or more applications configured to manage phone calls and/or text messages. Sensor data can include data from (for example) an accelerometer, magnetometer, gyroscope, GPS receiver and/or access-point receiver. The communication data and/or sensor data can include a data stream, time-series data, one or more statistics, one or more discrete measurements, and so on.

At block 830, the particular electronic device may process the one or more data sets using a trained model to generate a result corresponding to a risk of heart failure. For example, a processor of the particular electronic device may execute a trained machine learning model using the data sets as input. The output or result of the execution of the trained model may include or may predict a category of heart failure risk, an estimated probability that the user will suffer heart failure and/or an estimated health-status score (e.g., KCCQ score). In some instances, the output or result may be further processed (e.g., to compare an estimated KCCQ score to one or more thresholds). After processing of the data sets, a classification can be generated that corresponds to (for example) one of a set of physiological meanings, such as a high risk of heart failure, a moderate risk of heart failure, a low risk of heart failure, or a designation lying therebetween. Similarly, the result may predict an estimated probability of heart failure rather than producing a categorical designation.

The machine learning model may be of a number of different types of supervised machine learning suitable for classification of input into categories or groups. Neural networks, boosted trees, decision trees, hidden Markov models, linear regressions, and support vector machines may be particularly useful in classifying the collected data sets as belonging to category of heart failure risk and/or a probability of a user's risk of heart failure. In some embodiments, the trained model may be trained using subject survey data (e.g., KCCQ data) and passively collected data (e.g., sensor data and/or communication data). The survey data may correspond to input received at the particular electronic device or received from another device (e.g., a device of a person who administered a survey). The training data may have corresponded to a same user and/or device associated with the data sets received at block 820 and/or other users and/or other devices.

In addition to regression analysis, a classification analysis with a K-Nearest Neighbors (K-NN) approach may be performed after quantizing KCCQ summary scores. Data were dichotomized into KCCQ scores less than or equal to 25 or >25. KCCQ scores less than or equal to 25 correspond to New York Heart Association (NYHA) class IV. Subjects with class IV heart failure are unable to complete any physical activity without discomfort. KCCQ scores >25 correspond to NYHA class I-III which describes less severe heart failure compared to class IV. Clustering analysis may be performed for two subjects who had enough KCCQ summary scores in each class. The cosine distance and five nearest neighbors were used as model specifications. Five-fold cross validation (CV) may be implemented whereby the machine-learning model may be trained on four folds and the fifth held-out fold may be used for testing, and this process may be repeated for the remaining four folds. The percentage of correctly classified points were reported for each subject.

Optionally, in block 840, the particular electronic device may determine that an alert condition is satisfied based on the result. For example, the alert condition may be configured to be satisfied upon detecting that the result corresponds to one or more pre-specified categories (e.g., high risk) The alert condition may be thought of as a determination that the user is a substantial risk of heart failure. If met, the alert condition may trigger one or more actions by a processor of the particular electronic device.

In response to determining that an alert condition is satisfied based on the result the particular electronic device may, at block 850, output the result. For example, the particular electronic device may transmit the result to another electronic device, such as an electronic device of a caregiver, medical facility, monitoring service, or hospital. The result may be received by the other electronic device and may enable a caregiver or physician to determine whether admission to a hospital is likely or if further medical care is warranted. Caregivers and physicians may proactively contact the user to recommend changes in a plan of treatment. The other electronic device may also communicate to the particular electronic device that a frequency or scope of passive monitoring (i.e., data set collection) should be adjusted based on the received result. In this manner, the monitoring of sensor outputs may be updated to ensure that caregivers and physicians receive an appropriate amount of granularity in subject monitoring and heart failure risk predication. This may enable preemption of negative trends in subject health status or preparation for admission of a user into a medical facility or hospital.

In response to determining that an alert condition is not satisfied based on the result the particular electronic device may return to block 820 and continue monitoring the output of sensors to collect data sets.

Figure 9A:
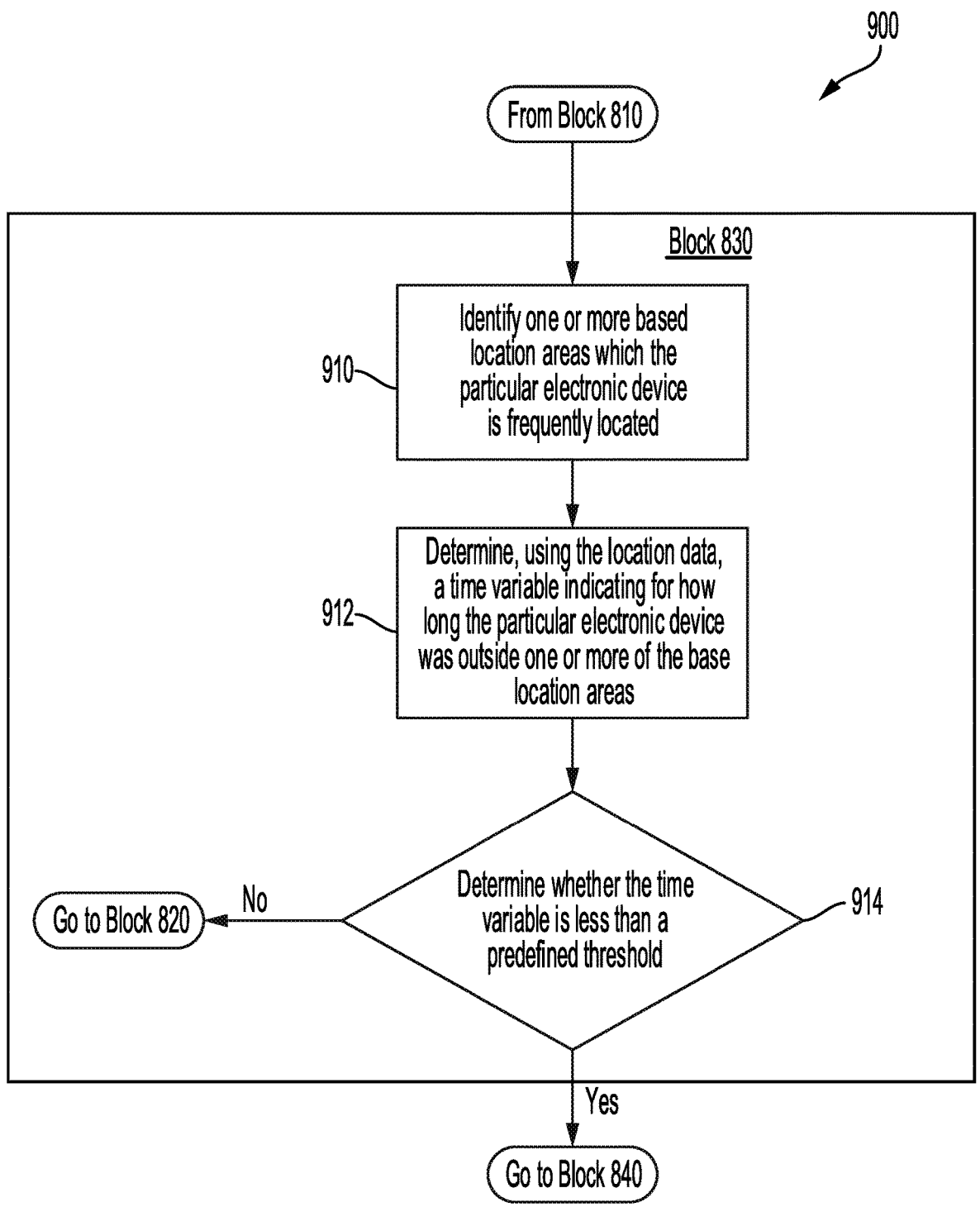
FIG. 9A is a process flow diagram of an embodiment method for monitoring location data for processing by machine-learning models to generate event predictions.
Figure 9B:
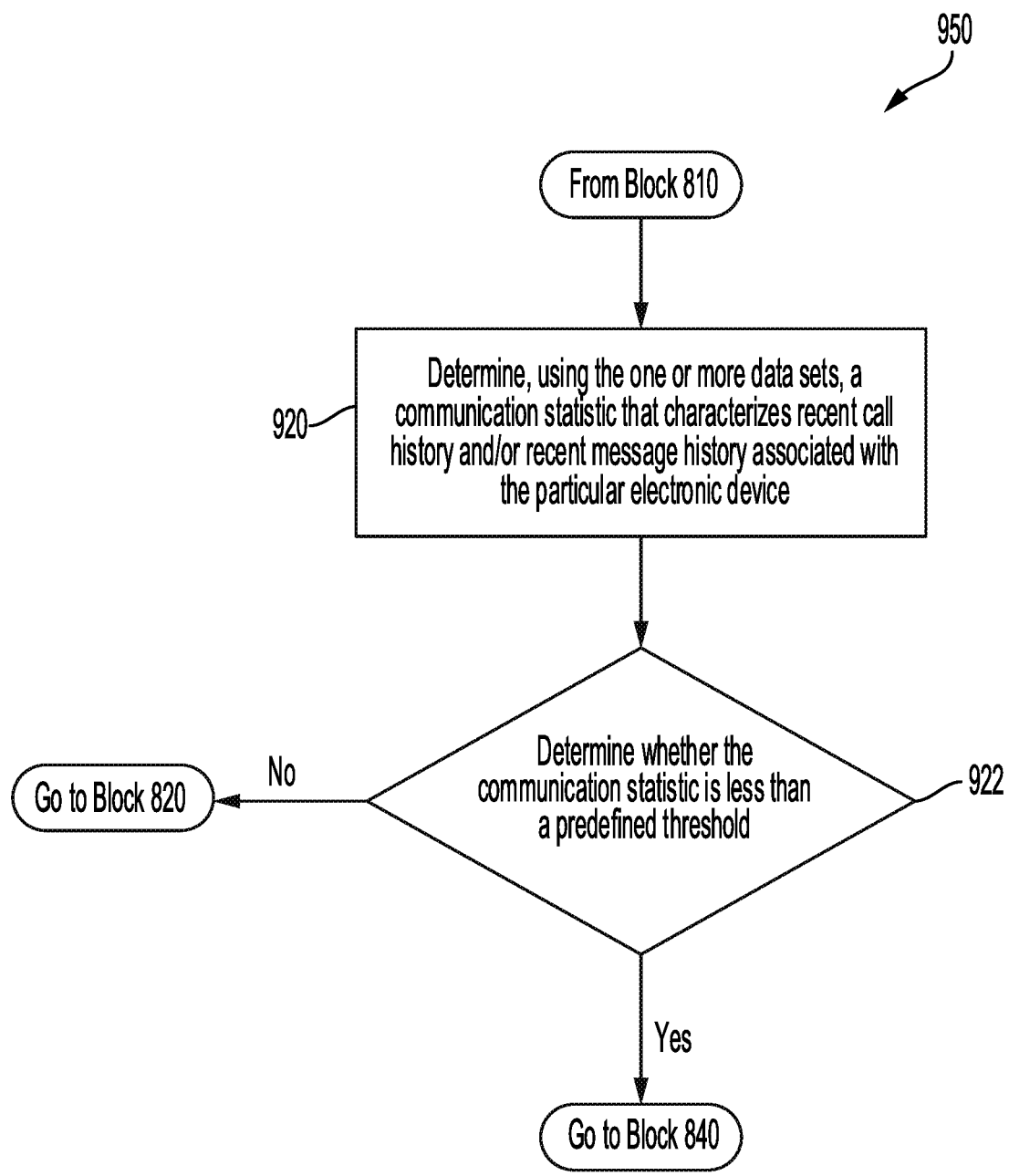
FIG. 9B is a process flow diagram of an embodiment method for monitoring a communication statistic for processing by machine-learning models to generate event predictions.
Figure 9C:
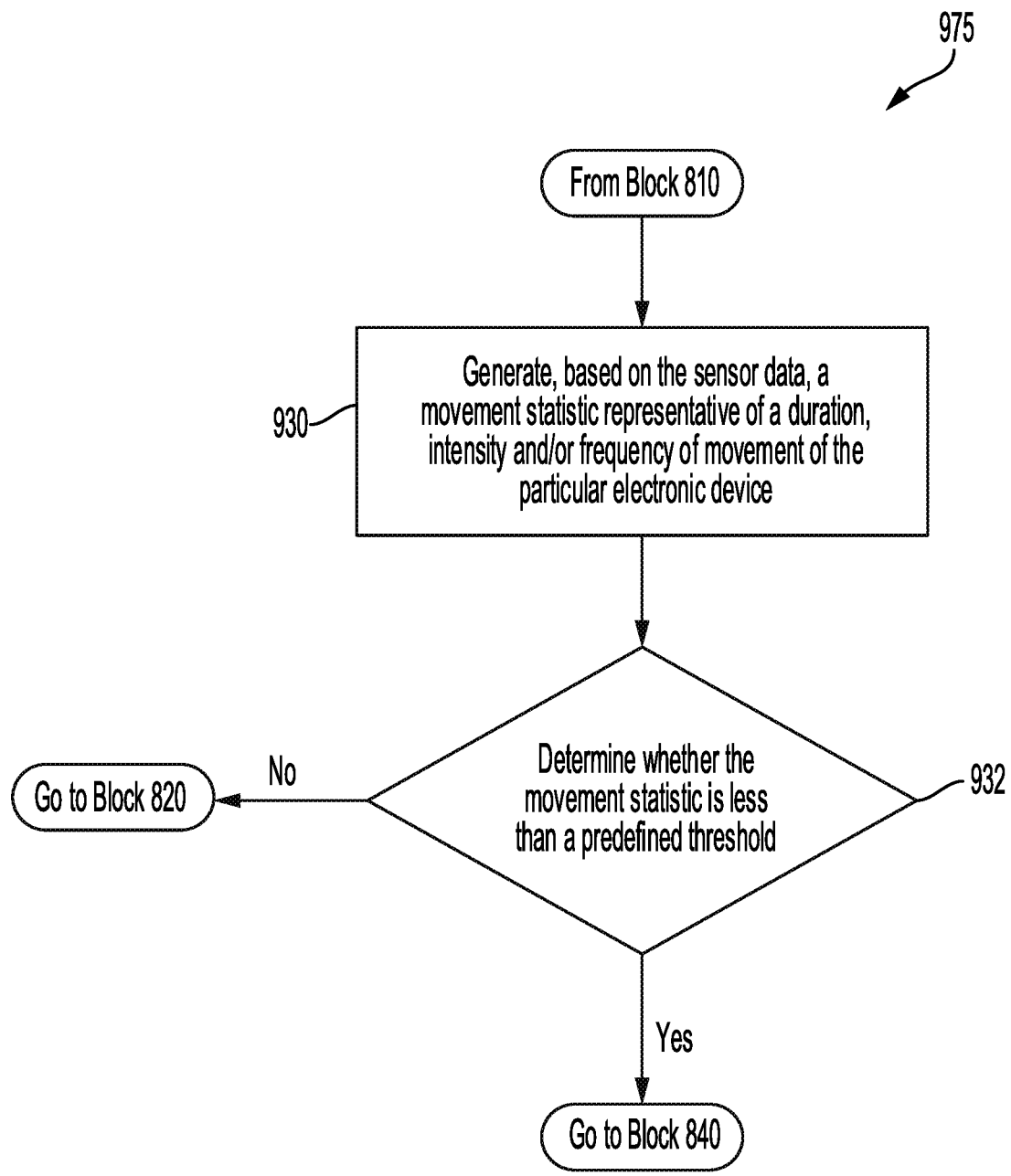
FIG. 9C is a process flow diagram of an embodiment method for monitoring movement data for processing by machine-learning models to generate event predictions.

FIGS. 9A-9C illustrates processes 900, 950, and 975 for the collection of data sets from various sensors of a particular electronic device. Processes 900, 950 and 975 can relate to techniques for analyzing different types of data using a threshold approach. A result of the analysis may indicate (for example) whether to present or transmit an alert. Thus, each of processes 900, 950 and 975 can correspond to or can replace blocks 830 and/or 840 in process 800.

Referring to FIG. 9A there is illustrated, an embodiment method 900 for monitoring location data to produce a result corresponding to a risk of heart failure. In method 900, the one or more data sets may include location data that identifies one or more locations at which the particular electronic device is located. Location data may be obtained using (for example) accelerometer output, GPS readings, dead reckoning, and/or other location-determination techniques. Theses sensors and feedback mechanisms may be used to determine how far and/or frequently a user travels from a home location and the range of places visited.

In block 910, the particular electronic device may identify one or more base location areas within which the particular electronic device is frequently located. For example, the particular electronic device may look at historical location data for the particular electronic device and identify locations in which the user is located for long periods of time on a semi-regular basis. In a non-limiting example, the particular electronic device may analyze historical location data and determine that any location in which the user may be located for a period of 5 hours or more on at least 10 occasions within a month period, is a base location. Base locations may correspond to work, home, or other place in which the user visits frequently and remains there for substantial amounts of time.

In block 912, the particular electronic device may determine, using the location data, a time variable indicating for how long the particular electronic device may be outside of the one or more base location areas. For example, the processor of the particular electronic device may compare locations visited by the user to the identified base locations to identify other locations. Upon identifying another location, the processor may track the amount of time spent by the user in the other location. In some embodiments, the time variable may be the length of time spent away from all base locations. Thus, the time variable may be the aggregate length of time during which the user may be located in other locations that are not base locations. Another time variable may be the time spent in transit between base locations.

In block 914, the particular electronic device may determine that the time variable is less than a predefined threshold. For example, the processor of particular electronic device may compared to the calculated time variable to a stored predefined threshold. The predefined threshold may be set by a software application operating on the particular electronic device or may be customized for the user. Physicians may set a threshold level of acceptable "roaming" for the user. This information may be provided via a server 110 of a hospital or medical facility. The predefined threshold may be included in a subject record stored on server 110, which may communicate the predefined threshold directly or provide this information by hosting a database accessible via the software application operating on the particular electronic device. The result is defined to correspond to a higher risk of heart failure when the time variable is less than the predefined threshold as compared to when the time variable exceeds the predefined threshold.

In response to determining that the time variable is less than the predefined threshold, the particular electronic device may return to block 840 of FIG. 8. Conversely, if the particular electronic device determines that the time variable is not less than the predefined threshold, it may return to block 820 of FIG. 8 and continue monitoring sensor output to collect data sets.

FIG. 9B illustrates an embodiment method 950 for monitoring a communication statistic to produce a result corresponding to a risk of heart failure. In method 950, the one or more data sets may include communication data relating to and characterizing a user's communications via the particular electronic device. Communication data may imply a level of communication activity by the user and the user's connection to friends and family. Communication data may includeany combination of a duration statistic of the one or more calls; a length statistic of the one or more outgoing messages; and/or a contact diversity statistic relating to a number of different contacts with which the one or more calls and/or the one or more outgoing messages were communicating.

In block 920, the particular electronic device may determine, using the one or more data sets, a communication statistic that characterizes recent call history and/or recent message history associated with the particular electronic device. For example, a processor of the particular electronic device may review call logs each day or over a period of time, history of incoming and outgoing text messages, messaging application activity and the like. Call logs may be reviewed to obtain the number of calls placed, the number of calls received, the number of different persons called or from which calls were received, as well as the duration of calls individually or on average. Text messages may be analyzed to determine the number of text messages, the number of people from whom messages were received or to whom messages were sent, and a length of messages. Messaging applications may or may not permit the accounting of correspondence. If a messaging application permits the processor to count messages sent and received, then these messages may be treated as text messages for the purposes of obtaining a count. If the messaging application does not permit analysis by the processor then the length of activity or usage of the application may be taken into account instead. The communication statistic may be derived using a function that contains variable associated with any combination of these measurements.

In block 922, the particular electronic device may determine the communication statistic is less than a predefined threshold. For example, the processor of particular electronic device may compared to the calculated communication statistic to a stored predefined threshold. The predefined threshold may be set by a software application operating on the particular electronic device or may be customized for the user. Physicians may use a threshold level of acceptable "social contact" for the user. This information may be provided via a server 110 of a hospital or medical facility. The predefined threshold may be included in a subject record stored on server 110, which may communicate the predefined threshold directly or provide this information by hosting a database accessible via the software application operating on the particular electronic device. The result is defined to correspond to a higher risk of heart failure when the communication statistic is less than the predefined threshold as compared to when the communication statistic exceeds the predefined threshold.

In response to determining that the communication statistic is less than the predefined threshold, the particular electronic device may return to block 840 of FIG. 8. Conversely, if the particular electronic device determines that the communication statistic is not less than the predefined threshold, it may return to block 820 of FIG. 8 and continue monitoring sensor output to collect data sets.

FIG. 9C illustrates an embodiment method 975 for monitoring movement data to produce a result corresponding to a risk of heart failure. In method 975, the one or more data sets may include communication data relating to and characterizing a user's movement and physical activity via the particular electronic device. Movement data may include a level of physical activity by the user or the structure of that movement. Magnetometers, accelerometers, cameras, and other sensors capable of detecting motion of providing raw output from which motion may be inferred, may be used to collect movement data. This data may be compared to a predefined threshold to determine whether the user's physical activity level meets a desired level. Thus, the one or more data sets includes sensor data characterizing movement of the particular electronic device.

In block 930, the particular electronic device may generate, based on the sensor data, a movement statistic representative of a duration, intensity, structure and/or frequency of movement of the particular electronic device. For example, the particular electronic device may leverage one or more of a magnetometer, an accelerometer, a camera or other imaging sensor to determine that the computing device is in motion. The processor of the particular electronic device may capture this output and store it until such time as the processor determines that the computing device is no longer in motion. Alternatively, the processor may merely record a length of time during which the computing device is in motion. The movement statistic may include an aggregate amount of time during which the user may be in motion, or may be more granular, indicating durations of time considered to include "high energy activity" and "low energy activity". The movement statistic may be derived using a function that accounts or the movement data variables and outputs a duration of time or a percentage of time spent active.

In block 932, the particular electronic device may determine the movement statistic is less than a predefined threshold. For example, the processor of particular electronic device may compared the calculated movement statistic to a stored predefined threshold. The predefined threshold may be set by a software application operating on the particular electronic device or may be customized for the user. Physicians may use a threshold level of acceptable "physical activity" for the user. This information may be provided via a server 110 of a hospital or medical facility. The predefined threshold may be included in a subject record stored on server 110, which may communicate the predefined threshold directly or provide this information by hosting a database accessible via the software application operating on the particular electronic device. The result is defined to correspond to a higher risk of heart failure when the movement statistic is less than the predefined threshold as compared to when the movement statistic exceeds the predefined threshold.

In response to determining that the movement statistic is less than the predefined threshold, the particular electronic device may return to block 840 of FIG. 8. Conversely, if the particular electronic device determines that the movement statistic is not less than the predefined threshold, it may return to block 820 of FIG. 8 and continue monitoring sensor output to collect data sets.

Figure 10:
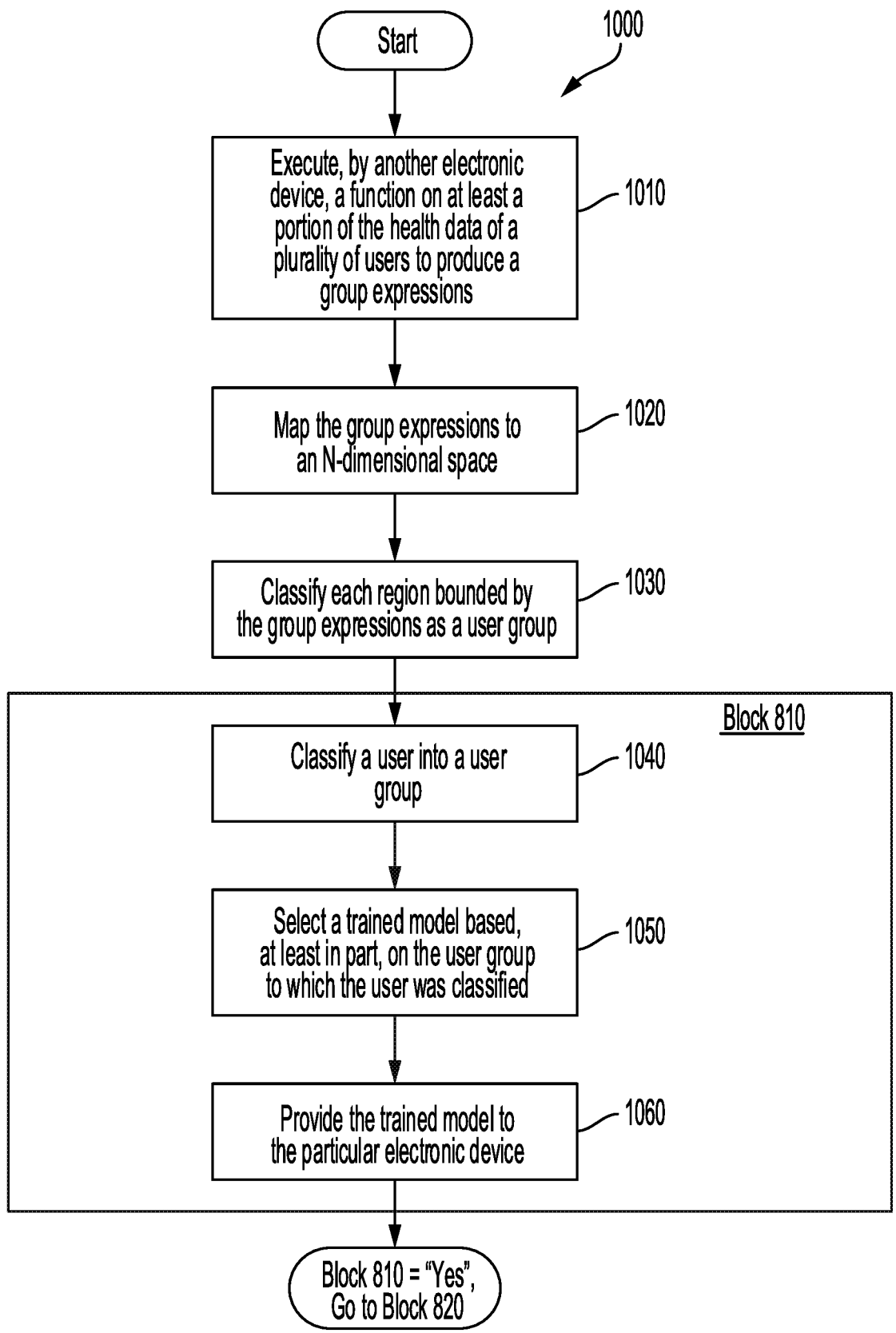
FIG. 10 is a process flow diagram of an embodiment method for constructing a machine-learning model to generate event predictions.

FIG. 10 illustrates an embodiment method 1000 for constructing a machine-learning model for classifying a user's risk of heart failure. With reference to FIGS. 1-10, the computing device 102 or the server 110 or a third party may generate and train a machine-learning model for predicting a risk of heart failure based, at least in part, on passively collected sensor output of the computing device 102. The trained model may be used by the particular electronic device (e.g. computing device 102) to determine whether the risk of heart failure is sufficient to trigger an alert condition.

The method 1000 may include creating, by another electronic device, a user classification model based at least in part on health data for a plurality of users; wherein determining that data is to be monitored at the particular electronic device for predictions of heart failure may include classifying, by the another electronic device, a user into a user group using the user-specific classification model; selecting, by the another electronic device, a trained model based, at least in part, on the user group to which the user may be classified; and providing, by the another electronic device, the trained model to the particular electronic device. The method may further include executing, by another electronic device, a function on at least a portion of the health data of the plurality of users to produce group expressions; mapping, by another electronic device, the group expressions to an N-dimensional space; and classifying, by the another electronic device, each region bounded by the group expressions as a user group.

It will be appreciated that the techniques for passive monitoring of behavioral and locomotor behavior by an electronic device, described with reference to inferring or predicting events (e.g., worsening of heart failure symptoms), may be applicable to the inference or prediction of other conditions and health events. For example, the passive monitoring of sensor output characteristic of behavioral and locomotor activity patterns may be used to predict the onset of Alzheimer's disease, depression, neurological conditions, stoke, pneumonia, dementia, chronic pulmonary disorders, muscular disease, and the like. The techniques described herein may be applied to the prediction of a user's level of risk for a medical condition such as those described above, as well as the prediction of readmission to medical facility based on the worsening a pre-existing medical condition. Thus the techniques described herein may be used to predict the likelihood of the existence of a health condition as well as the likelihood that an existing health condition has deteriorated and requires further medical attention.

The attached appendix is herein incorporated to provide additional detail as to the scope of the various embodiments.

The foregoing method descriptions and the process flow diagrams are provided merely as illustrative examples and are not intended to require or imply that the operations of various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

While the terms "first" and "second" are used herein to describe data transmission associated with a subscription and data receiving associated with a different subscription, such identifiers are merely for convenience and are not meant to limit various embodiments to a particular order, sequence, type of network or carrier.

Various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such embodiment decisions should not be interpreted as causing a departure from the scope of the claims.

The hardware used to implement various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, (e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more example embodiments, the functions described may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

What is claimed is:

1. A computer-implemented method comprising:
   determining that data is to be monitored at a particular electronic device for indications of an event; and
   in response to the determination:
      accessing one or more data sets representative of one or more inputs or sensor measurements collected from one or more input devices or sensors of the particular electronic device, wherein the one or more data sets comprise communication data indicating communication interaction of a user associated with the particular electronic device with other users;
      processing the one or more data sets using a trained machine-learning model to generate a result corresponding to a predicted risk of the event;
      transmitting the result to a remote computing device;
      reconfiguring, based on an instruction received from the remote computing device, the particular electronic device to change an operation of the particular electronic device for collecting the inputs or sensor measurements;
      collecting additional input data or sensor measurements from the one or more input devices or sensors; and
      processing the additional input data or sensor measurements using the trained machine-learning model to generate an updated result corresponding to an updated risk of the event.

2. The computer-implemented method of claim 1, wherein the one or more data sets includes location data that identifies one or more locations at which the particular electronic device was located, and wherein processing the one or more data sets comprises:
   identifying one or more base location areas within which the particular electronic device has been frequently located;

determining, using the location data, a time variable indicating for how long the particular electronic device was outside of the one or more base location areas; and
inputting an input data set that includes the time variable to the trained machine-learning model.

3. The computer-implemented method of claim 1, wherein the communication data comprise data pertaining to one or more of phone calls, messages, or a de-identified contact list, and wherein processing the one or more data sets comprises:
determining, using the communication data in the one or more data sets, a communication statistic that characterizes recent call history or recent message history associated with the particular electronic device; and
inputting an input data set that includes the communication statistic to the trained machine-learning model.

4. The computer-implemented method of claim 3, wherein the communication statistic comprises one or more of:
a count of one or more of the phone calls or outgoing messages;
a duration statistic of the one or more calls;
a length statistic of the one or more outgoing messages; or
a contact diversity statistic relating to a number of different contacts with which the one or more calls or outgoing messages were communicating.

5. The computer-implemented method of claim 1, wherein the sensor measurements characterize movement of the particular electronic device, and wherein processing the one or more data sets comprises:
generating, based on the sensor measurements, a movement statistic representative of one or more of a duration, an intensity or a frequency of movement of the particular electronic device; and
inputting an input data set that includes the movement statistic to the trained machine-learning model.

6. The computer-implemented method of claim 1, further comprising:
determining that an alert condition is satisfied based on the result; and
as a result of determining that the alert condition is satisfied, transmitting the result to another electronic device.

7. The computer-implemented method of claim 1, further comprising:
accessing, by another electronic device, a user classification model based at least in part on health data for a plurality of users;
wherein determining that data is to be monitored at the particular electronic device for predictions of the event comprises:
classifying, by the other electronic device, a user into a user group using the user classification model; and
selecting, by the other electronic device, the trained machine-learning model based at least in part on the user group to which the user is classified.

8. The computer-implemented method of claim 7, further comprising:
executing, by the other electronic device, a function on at least a portion of the health data of the plurality of users to produce group expressions;
mapping, by the other electronic device, the group expressions to an N-dimensional space; and
classifying, by the other electronic device, a region bounded by the group expressions as a user group.

9. The computer-implemented method of claim 1, wherein the trained machine-learning model is trained a machine-learning model with health record data of a user associated with the particular electronic device.

10. A computer-program product tangibly embodied in a non-transitory machine-readable storage medium, including instructions configured to cause one or more data processors to perform operations including:
determining that data is to be monitored at a particular electronic device for indications of an event; and
in response to the determination:
accessing one or more data sets representative of one or more inputs or sensor measurements collected from one or more input devices or sensors of the particular electronic device, wherein the one or more data sets comprise communication data indicating communication interaction of a user associated with the particular electronic device with other users;
processing the one or more data sets using a trained machine-learning model to generate a result corresponding to a predicted risk of the event;
transmitting the result to a remote computing device;
reconfiguring, based on an instruction received from the remote computing device, the particular electronic device to change an operation of the particular electronic device for collecting the inputs or sensor measurements;
collecting additional input data or sensor measurements from the one or more input devices or sensors; and
processing the additional input data or sensor measurements using the trained machine-learning model to generate an updated result corresponding to an updated risk of the event.

11. The computer-program product of claim 10, wherein the one or more data sets includes location data that identifies one or more locations at which the particular electronic device was located, and wherein processing the one or more data sets comprises:
identifying one or more base location areas within which the particular electronic device has been frequently located;
determining, using the location data, a time variable indicating for how long the particular electronic device was outside of the one or more base location areas; and
inputting an input data set that includes the time variable to the trained machine-learning model.

12. The computer-program product of claim 10, wherein the communication data comprise data pertaining to one or more of phone calls, text messages, or a de-identified contact list, and wherein processing the one or more data sets comprises:
determining, using the communication data in the one or more data sets, a communication statistic that characterizes recent call history or recent message history associated with the particular electronic device; and
inputting an input data set that includes the communication statistic to the trained machine-learning model.

13. The computer-program product of claim 12, wherein the communication statistic comprises one or more of:
a count of one or more of the phone calls or outgoing messages;
a duration statistic of the one or more calls;
a length statistic of the one or more outgoing messages; or
a contact diversity statistic relating to a number of different contacts with which the one or more calls or the one or more outgoing messages were communicating.

14. The computer-program product of claim 10, wherein the sensor measurements characterize movement of the particular electronic device, and wherein processing the one or more data sets comprises:
- generating, based on the sensor measurements, a movement statistic representative of one or more of a duration, an intensity, or a frequency of movement of the particular electronic device; and
- inputting an input data set that includes the movement statistic to the trained machine-learning model.

15. The computer-program product of claim 10, wherein the instructions further cause the one or more data processors to perform operations including:
- determining that an alert condition is satisfied based on the result; and
- as a result of determining that the alert condition is satisfied, transmitting the result to another electronic device.

16. The computer-program product of claim 10, wherein the instructions further cause the one or more data processors to perform operations including:
- accessing, by another electronic device, a user classification model based at least in part on health data for a plurality of users;
- wherein determining that data is to be monitored at the particular electronic device for predictions of the event comprises:
  - classifying, by the other electronic device, a user into a user group using the user classification model; and
  - selecting, by the other electronic device, the trained machine-learning model based at least in part on the user group to which the user is classified.

17. The computer-program product of claim 16, wherein the instructions further cause the one or more data processors to perform operations including:
- executing, by the other electronic device, a function on at least a portion of the health data of the plurality of users to produce group expressions;
- mapping, by the other electronic device, the group expressions to an N-dimensional space; and
- classifying, by the other electronic device, a region bounded by the group expressions as a user group.

18. The computer-program product of claim 10, wherein the trained machine-learning model is trained a machine-learning model with health record data of a user associated with the particular electronic device.

19. A system comprising:
- one or more data processors; and
- a non-transitory computer readable storage medium containing instructions which when executed on the one or more data processors, cause the one or more data processors to perform operations including:
  - determining that data is to be monitored at a particular electronic device for indications of an event; and
  - in response to the determination:
    - accessing one or more data sets representative of one or more inputs or sensor measurements collected from one or more input devices or sensors of the particular electronic device, wherein the one or more data sets comprise communication data indicating communication interaction of a user associated with the particular electronic device with other users;
    - processing the one or more data sets using a trained machine-learning model to generate a result corresponding to a predicted risk of the event;
    - transmitting the result to a remote computing device;
    - reconfiguring, based on an instruction received from the remote computing device, the particular electronic device to change an operation of the particular electronic device for collecting the inputs or sensor measurements;
    - collecting additional input data or sensor measurements from the one or more input devices or sensors; and
    - processing the additional input data or sensor measurements using the trained machine-learning model to generate an updated result corresponding to an updated risk of the event.

20. The system of claim 19, wherein the one or more data sets includes location data that identifies one or more locations at which the particular electronic device was located, and wherein processing the one or more data sets comprises:
- identifying one or more base location areas within which the particular electronic device has been frequently located;
- determining, using the location data, a time variable indicating for how long the particular electronic device was outside of the one or more base location areas; and
- inputting an input data set that includes the time variable to the trained machine-learning model.

21. The system of claim 19, wherein the communication data comprise data pertaining to one or more of phone calls, text messages, or a de-identified contact list, and wherein processing the one or more data sets comprises:
- determining, using the communication data in the one or more data sets, a communication statistic that characterizes recent call history or recent message history associated with the particular electronic device; and
- inputting an input data set that includes the communication statistic to the trained machine-learning model.

22. The system of claim 21, wherein the communication statistic comprises one or more of:
- a count of one or more of the phone calls or outgoing messages;
- a duration statistic of the one or more calls;
- a length statistic of the one or more outgoing messages; or
- a contact diversity statistic relating to a number of different contacts with which the one or more calls or the one or more outgoing messages were communicating.

23. The system of claim 19, wherein the sensor measurements characterize movement of the particular electronic device, and wherein processing the one or more data sets comprises:
- generating, based on the sensor measurements, a movement statistic representative of one or more of a duration, an intensity, or a frequency of movement of the particular electronic device; and
- inputting an input data set that includes the movement statistic to the trained machine-learning model.

24. The system of claim 19, wherein the instructions further cause the one or more data processors to perform operations including:
- determining that an alert condition is satisfied based on the result; and
- as a result of determining that the alert condition is satisfied, transmitting the result to another electronic device.

25. The system of claim 19, wherein the instructions further cause the one or more data processors to perform operations including:

accessing, by another electronic device, a user classification model based at least in part on health data for a plurality of users;

wherein determining that data is to be monitored at the particular electronic device for predictions of the event comprises:

classifying, by the other electronic device, a user into a user group using the user classification model; and selecting, by the other electronic device, the trained machine-learning model based at least in part on the user group to which the user is classified.

26. The system of claim 25, wherein the instructions further cause the one or more data processors to perform operations including:

executing, by the other electronic device, a function on at least a portion of the health data of the plurality of users to produce group expressions;

mapping, by the other electronic device, the group expressions to an N-dimensional space; and classifying, by the other electronic device, a region bounded by the group expressions as a user group.

27. The system of claim 19, wherein the trained machine-learning model is trained a machine-learning model with health record data of a user associated with the particular electronic device.

* * * * *